(12) United States Patent
Mack

(10) Patent No.: US 9,175,268 B2
(45) Date of Patent: *Nov. 3, 2015

(54) METHODS FOR THE PRODUCTION OF IPS CELLS

(75) Inventor: Amanda Mack, Madison, WI (US)

(73) Assignee: Cellular Dynamics International, Inc., Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/539,366

(22) Filed: Aug. 11, 2009

(65) Prior Publication Data

US 2010/0041054 A1    Feb. 18, 2010

Related U.S. Application Data

(60) Provisional application No. 61/088,054, filed on Aug. 12, 2008.

(51) Int. Cl.
    *C12N 5/074* (2010.01)

(52) U.S. Cl.
    CPC ........ *C12N 5/0696* (2013.01); *C12N 2501/602* (2013.01); *C12N 2501/603* (2013.01); *C12N 2501/605* (2013.01); *C12N 2501/608* (2013.01); *C12N 2510/00* (2013.01); *C12N 2799/027* (2013.01)

(58) Field of Classification Search
    CPC ........... C12N 5/0696; C12N 2501/602; C12N 2501/605; C12N 2501/608; C12N 2510/00; C12N 2799/027
    See application file for complete search history.

(56) References Cited

U.S. PATENT DOCUMENTS

| | | | |
|---|---|---|---|
| 5,925,565 A | 7/1999 | Berlioz et al. | 435/325 |
| 5,935,819 A | 8/1999 | Eichner et al. | 435/69.4 |
| 6,060,273 A | 5/2000 | Wilhelm et al. | |
| 7,465,580 B2 | 12/2008 | Sugden et al. | |
| 7,682,828 B2 | 3/2010 | Jaenisch et al. | 435/455 |
| 8,058,065 B2 * | 11/2011 | Yamanaka et al. | 435/377 |
| 8,183,038 B2 | 5/2012 | Thomson et al. | |
| 8,268,620 B2 | 9/2012 | Thomson et al. | |
| 8,440,461 B2 | 5/2013 | Thomson et al. | |
| 2002/0090722 A1 | 7/2002 | Dominko et al. | |
| 2002/0136709 A1 | 9/2002 | Zahner et al. | |
| 2004/0199935 A1 | 10/2004 | Chapman | |
| 2005/0079616 A1 | 4/2005 | Reubinoff | |
| 2005/0255573 A1 | 11/2005 | Chambers et al. | |
| 2005/0260564 A1 | 11/2005 | Sugden et al. | |
| 2006/0110830 A1 | 5/2006 | Dominko et al. | |
| 2006/0128018 A1 | 6/2006 | Zwaka et al. | |
| 2006/0160218 A1 | 7/2006 | Slack et al. | |
| 2006/0263882 A1 | 11/2006 | Fazio et al. | 435/455 |
| 2008/0003560 A1 | 1/2008 | Nakatsuji et al. | |
| 2008/0233610 A1 | 9/2008 | Thomson et al. | |
| 2009/0047263 A1* | 2/2009 | Yamanaka et al. | 424/93.21 |
| 2009/0191159 A1 | 7/2009 | Sakurada et al. | |
| 2010/0003757 A1* | 1/2010 | Mack et al. | 435/455 |
| 2010/0184227 A1 | 7/2010 | Thomson et al. | |
| 2010/0279404 A1 | 11/2010 | Yamanaka et al. | |
| 2010/0285589 A1* | 11/2010 | Lowry et al. | 435/455 |
| 2011/0217274 A1 | 9/2011 | Reld | |
| 2013/0189778 A1 | 7/2013 | Mack | |
| 2013/0210138 A1 | 8/2013 | Thomson et al. | |
| 2013/0217117 A1 | 8/2013 | Thomson et al. | |
| 2014/0038293 A1 | 2/2014 | Mack | |
| 2014/0057355 A1 | 2/2014 | Thomson et al. | |

FOREIGN PATENT DOCUMENTS

| | | |
|---|---|---|
| CA | 2660123 | 10/2008 |
| EP | 1698639 | 9/2006 |
| EP | 2048229 | 4/2009 |
| EP | 2053128 | 4/2009 |
| EP | 2 072 618 | 6/2009 |
| JP | 8-502644 | 3/1996 |
| JP | 10-113178 | 6/1998 |
| JP | 2007-209240 | 8/2007 |
| JP | 2007-525975 | 9/2007 |
| JP | 2007-535923 | 12/2007 |
| JP | 2008-067693 | 3/2008 |
| WO | WO 2005/072129 | 8/2005 |
| WO | WO 2005/108585 | 11/2005 |
| WO | WO 2007/047766 | 4/2007 |
| WO | WO 2007/069666 | 6/2007 |
| WO | WO 2008-013067 | 1/2008 |
| WO | WO 2008-013737 | 1/2008 |
| WO | WO 2008-033469 | 3/2008 |
| WO | WO 2008/118820 | 10/2008 |
| WO | WO 2009/032194 | 3/2009 |
| WO | WO 2009/032456 | 3/2009 |
| WO | WO 2009/061442 | 5/2009 |
| WO | WO 2009/091543 | 7/2009 |
| WO | WO 2009/092042 | 7/2009 |
| WO | WO 2009/133971 | 11/2009 |

(Continued)

OTHER PUBLICATIONS

Lois et al. Science 295: 868-872, 2002.*
pMXs Retroviral Vector data sheet, accessed online at www.cellbiolabs.com on Jan. 21, 2011.*
Hermeking et al. PNAS, 97(5): 2229-2234, 2000.*
He et al. PNAS, 95: 2509-2514, 1998.*
Graham et al. Neuron, 39: 746-765, Aug. 2003.*
"pIRES2-EGFP vector information" accessed at www.clontech.com on Jan. 24, 2011.*
Yoshimizu et al. Develop. Growth. Diff., 41: 675-684, 1999.*
Yeom et al. Development, 122: 881-894, 1996.*
"pBluescript II XR predigested vector" instruction manual, accessed at http://www.genomics.agilent.com/files/Manual/212240.pdf on Jan. 24, 2011.*
Oster et al. Mol. Cell. Biology, 20(18): 6768-6778, 2000.*
"pBABE-MN-IRES-E-GFP" vector information accessed online at http://www.lablife.org/p?a=vdb_view&id=g2.
CylnpjjVjRDXWTUIiXTHEX8hmr0-, accessed online on Jan. 24, 2011, pp. 1-2.*
"pLIB vector information" accessed online at www.clontech.com on Jan. 24, 2011, pp. 1-2.*

(Continued)

*Primary Examiner* — Thaian N Ton
(74) *Attorney, Agent, or Firm* — Parker Highlander PLLC

(57) ABSTRACT

Methods and composition of induction of pluripotent stem cells are disclosed. For example, in certain aspects methods for generating induced pluripotent stem cells using reporter genes are described. Furthermore, the invention provides novel reprogramming vectors employing reporter genes.

22 Claims, 1 Drawing Sheet

(56) References Cited

FOREIGN PATENT DOCUMENTS

| | | |
|---|---|---|
| WO | WO 2009-149233 | 12/2009 |
| WO | WO 2010-012077 | 2/2010 |
| WO | WO 2010/028019 | 3/2010 |

OTHER PUBLICATIONS

Ren et al. Stem Cells, 24(5): 1338-1347, 2006.*
Baker. Nature Reports Stem Cells, pp. 1-2, published online Jun. 7, 2007, accessed online at http://www.nature.com/stemcells/2007/0706/070607/full/stemcells.2007.9.html on Oct. 18, 2012.*
Chang et al., "Polycistronic lentiviral vectore for "Hit and Run" reprogramming of adult skin fibroblasts to induced pluripotent stem cells," *Stem Cells*, 27:1042-1049, 2009.
International Search Report and Written Opinion, issued in International Application No. PCT/US2009/053403, mail date Dec. 2, 2009.
Lowry et al., "Generation of human induced pluripotent stems cells from dermal fibroblasts," *PNAS*, 105(8):2883-2888, 2008.
Okita et al., "Generation of germline-competent induced pluripotent stem cells," *Nature*, 448:313-318, 2007.
Shao et al., "Generation of iPS cells using defined factors linked via the self-cleaving 2A sequences in a single open reading frame," *Cell Research*, 19:296-306, 2009.
Sommer et al., "Induced pluripotent stem cell generation using a single lentiviral stem cell cassette," *Stem Cells*, 27:543-549, 2009.
Boyer et al., "Core transcriptional regulatory circuitry in human embryonic stem cells," *Cell*, 122 (6): 947-956, 2005.
Brambrink et al., "Sequential expression of pluripotency markers during direct reprogramming of mouse somatic cells," *Cell Stem Cell*, 2 (2) 151-159, 2008.
Carey et al., "Reprogramming of murine and human somatic cells using a single polycistronic vector," *PNAS USA*, 106 (1): 157-162, 2009.
Chambers et al., "Functional expression cloning of Nanog, a pluripotency sustaining factor in embryonic stem cells," *Cell*, 113 (5): 643-655, 2003.
Jaenisch, "Transgenic animals," *Science*, 240 (4858): 1468-1474, 1988.
Kim et al., "Construction of a bifunctional mRNA in the mouse by using the internal ribosomal entry site of the encephalomyocarditis virus," *Mol. Cellular Biol.*, 12 (8): 3636-3643, 1992.
Macejak and Sarnow, "Internal initiation of translation mediated by the 5' leader of a cellular mRNA," *Nature*, 353 (6339): 90-94, 1991.
McBratney et al., "Internal initiation of translation," *Curr. Opin. Cell Biol.*, 5 (6): 961-965, 1993.
Mikkelsen et al., "Dissecting direct reprogramming through integrative genomic analysis," *Nature*, 454: 49-56, 2008.
Okita et al., "Generation of mouse induced pluripotent stem cells without viral vectors," *Science*, 322 (5903): 949-953, 2008.
Pelletier and Sonenberg, "Internal initiation of translation of eukaryotic mRNA directed by a sequence derived from poliovirus RNA," *Nature*, 334 (6180): 320-325, 1988.
Provost et al., "Viral 2A peptides allow expression of multiple proteins from a single ORF in transgenic zebrafish embryos," *Genesis*, 45 (10): 625-629, 2007.
Stadtfeld et al., "Induced pluripotent stem cells generated without viral integration," *Science*, 322 (5903): 945-949, 2008.
Takahashi et al., "Induction of pluripotent stem cells from adult human fibroblasts by defined factors," *Cell*, (5): 861-872, 2007.
Takahashi et al., "Induction of pluripotent stem cells from mouse embryonic and adult fibroblast cultures by defined factors," *Cell*, 126 (4): 663-676, 2006.
Wernig et al., "In vitro reprogramming of fibroblasts into a pluripotent ES-cell-like state," *Nature*, 448: 318-325, 2007.
Yu et al., "Induced pluripotent stem cell lines derived from human somatic cells," *Science*, 318: 1917-1920, 2007.
Aoi et al., "Generation of pluripotent stem cells from adult mouse liver and stomach cells," *Science*, 321:699-702, 2008.
Belloch et al., "Generation of induced pluripotent stem cells in the absence of drug selection," *Cell Stem Cell*, 1:245-247, 2007.

Cox and Rizzino, "Induced pluripotent stem cells: what lies beyond the paradigm shift," *Experimental Biology and Medicine*, 235:148-158, 2010.
Egli et al., "Mediators of reprogramming: transcription factors and transitions through mitosis," *Moecular Cell Biology*, 9:505-516, 2008.
Hanna et al., "Direct reprogramming of terminally differentiated mature B lymphocytes to pluripotency," *Cell*, 133:250-264, 2008.
Hanna et al., "Reprogramming of somatic cell identity," *Cold Spring Harbor Symposia on Quantitative Biology*, vol. 73: 147-155, 2008.
Huangfu et al., "Induction of pluripotent stem cells by defined factors in greatly improved by small-molecule compounds," *Nature Biotechnology*, 26:795-797, 2008.
Jia et al., "A nonviral minicircle vector for deriving human iPS cells," *Nature Methods*, 7(3):197-199, 2010.
Kim et al., "Pluripotent stem cells induced from adult neural stem cells by reprogramming with two factors," *Nature*, 454:646-650, 2008.
Lewitzky and Yamanaka, "Reprogramming somatic cells towards pluripotency by defined factors," *Current Opinion in Biotechnology*, 18:467-473, 2007.
Liao et al., "Enhanced efficiency of generating induced pluripotent stem (iPS) cells from human somatic cells by a combination of six transcription factors," *Cell Research*, 18:600-603, 2008.
Maherali et al., "Directly reprogrammed fibroblasts show global epigenetic remodeling and widespread tissue contribution," *Cell Stem Cell.*, 1:55-70, 2007.
Mali et al., "Improved efficiency and pace of generating induced pluripotent stem cells from human adult and fetal firoblasts," *Stem Cells*, 26:1998-2005, 2008.
Meissner et al., "Direct reprogramming of genetically unmodified fibroblasts into pluripotent stem cells," *Nature Biotechnology*, 25:1177-1181, 2007.
Nakagawa et al., "Generation of induced pluripotent stem cells with Myc from mouse and human fibroblasts," *Nature Biotechnology*, 26:101-106, 2008.
Papapetrou et al., "Stoichiometric and temporal requirements of Oct4, Sox2, K1f4, and c-Myc expression for efficient human iPSC induction and differentiation," *PNAS Early Edition*. Published online before print Jun. 23, 2009, doi: 10.1073/pnas.0904825106.
Park et al., "Disease-specific induced pluripotent stem cells," *Cell.*, 134:877-886, 2008.
Park et al., "Generation of human-induced pluripotent stem cells," *Nature Protocls*, 3:1180-1186, 2008.
Park et al., "Reprogramming of human somatic cells to pluripotency with defined factors," *Nature*, 451:141-147, 2008.
Shi et al., "A combined chemical and genetic approach for the generation of induced pluripotent stem cells," *Cell Stem Cell*, 2:525-528, 2008.
Stadtfeld et al., "Defining molecular cornerstones during fibroblasts to iPS cell reprogramming in mouse," *Cell Stem Cell*, 2:230-240, 2008.
Warren et al., "Highly efficient reprogramming to pluripotency and directed differentiation of human cells with synthetic modified mRNA," *Cell Stem Cell*, 7:1-13, 2010.
Wernig et al., "C-Myc is dispensable for direct reprogramming of mouse fibroblasts," *Cell Stem Cell*, 2(1):10-12, 2008.
Wernig et al., "A drug-inducible transgenic system for direct reprogramming of multiple somatc cell types," *Nature Biotechnology*, 26:916-924, 2008.
Yamanaka, "Induction of pluripotent stem cells from mouse fibroblasts by four transcription factors," *Cell Proliferation*, 41(Suppl. 1):51-56, 2008.
Office Communication issued in Chinese Patent Application No. 200980138340.8, dated Mar. 7. 2013.
Office Action issued in Japanese Application No. 2011-523094, mailed Jan. 17, 2014.
Tanabe et al., "Historical overview and future prospects of the iPS cells," *Regeneration Medicine*, 7(2):83-89, 2008.
Alberio et al., "Reprogramming somatic cells into stem cells," *Reproduction*, 132:709-720, 2006.

(56) References Cited

OTHER PUBLICATIONS

Amit et al., "Clonally derived human embryonic stem cell lines maintain pluripotency and proliferative potential for prolonged periods of culture," *Developmental Biology*, 227(2):271-278, 2000.
Avilion et al., "Multipotent cell lineages in early mouse development depend on SOX2 function," *Genes & Development*, 17:126-140, 2003.
Cibelli et al., "Cellular reprogramming for the creation of patient-specific embryonic stem cells," *Stem Cell Rev.*, 2:289-295, 2006.
Collas, "Dedifferentiation of cells: new approaches," *Cytotherapy*, 9(3):236-244, 2007.
Conese et al., "Gene therapy progress and prospects: episomally maintained self-replicating systems," *Gene Therapy*, 11(24):1735-1741, 2004.
Cowan et al., "Nuclear reprogramming of somatic cells after fusion with human embryonic stem cells science," *Science*, 309(5739):1369-1373, 2005.
Egli et al., "Developmental reprogramming after chromosome transfer into mitotic mouse zygotes," *Nature*, 447(7145):679-685, 2007.
Fackler, "Risk taking is in his genes," *The New York Times*, Dec. 11, 2007.
Frolov et al., "Alphavirus-based expression vectors: strategies and applications," *Proc. Natl. Acad. Sci. USA*, 93(21):11371-11377, 1996.
Gao et al., "Nonviral gene delivery: what we know and what is next," *The AAPS Journal*, 9(1):E92-E104, 2007.
Hellen and Wimmer, "Translation of encephalomyocarditis virus RNA by internal ribosomal entry," *Curr Top Microbiol Immunol.*, 203:31-63, 1995.
Hochedlinger and Jaenisch, "Nuclear reprogramming and pluripotency," *Nature*, 441(7097):1061-1067, 2006.
U.S. Appl. No. 90/020,068, Ex Parte Reexamination of U.S. Pat. No. 8,268,620, downloaded Jan. 15, 2015.
Ivanova et al., "Dissecting self-renewal in stem cells with RNA interference," *Nature*, 442(7102):533-538, 2006.
Jha et al., "SV40-mediated immortalization," *Experimental Cell Res.*, 245(1):1-7, 1998.
Kabouridis, "Biological applications of the protein transduction technology," *Trends in Biotechnology*, 21(11):498-503, 2003.
Kaji et al., "Virus-free induction of pluripotency and subsequent excision of reprogramming factors," *Nature*, 458(7239):771-775, 2009.
Ludwig et al., "Derivation of human embryonic stem cells in defined conditions," *Nature Biotechnology*, 24(2):185-187, 2006.
Ludwig et al., "Feeder-independent culture of human embryonic stem cells," *Nature Methods*, 3(8):637-646, 2006.
Mack, U.S. Appl. No. 61/058,858, filed Jun. 4, 2008.
Masaki et al., "Heterogeneity of pluripotent marker gene expression in colonies generated in human iPS cell induction culture," *Stem Cell Res.*, 1:105-115, 2007.
Milanesi et al., "BK virus-plasmid expression vector that persists episomally in human cells and shuttles into *Escherichia coli*,"*Molecular and Cellular Biology*, 4(8)1551-1560, 1984.
Nichols et al., "Characterization of a new human diploid cell strain, IMR-90," *Science*, 196(4285):60-63, 1977.
Nichols et al., "Formation of pluripotent stem cells in the mammalian embryo depends on the POU transcription factor Oct4," *Cell*, 95:379-391, 1998.
Office Action issued in Japanese Application No. 2011-512634, mailed Nov. 10, 2014, and English language translation thereof.
Office Action issued in U.S. Appl. No. 12/053,440, mailed Dec. 17, 2010.
Office Action issued in U.S. Appl. No. 12/053,440, mailed Dec. 18, 2012.
Office Action issued in U.S. Appl. No. 12/053,440, mailed Jun. 18, 2010.
Office Action issued in U.S. Appl. No. 12/053,440, mailed Jul. 25, 2012.
Office Action issued in U.S. Appl. No. 12/053,440, mailed May 20, 2011.

Office Action issued in U.S. Appl. No. 12/605,220, mailed Feb. 10, 2012.
Office Action issued in U.S. Appl. No. 12/605,220, mailed May 13, 2011.
Office Action issued in U.S. Appl. No. 12/727,061, mailed Jun. 15, 2011.
Office Action issued in U.S. Appl. No. 13/607,072, mailed Dec. 24, 2013.
Office Action issued in U.S. Appl. No. 13/607,072, mailed Jul. 17, 2014.
Office Action issued in U.S. Appl. No. 13/766,100, mailed Nov. 10, 2014.
Office Action issued in U.S. Appl. No. 13/793,594, mailed Jun. 19, 2014.
Office Action issued in U.S. Appl. No. 13/794,297, mailed Dec. 2, 2014.
Pralong et al., "Cell fusion for reprogramming pluripotency: toward elimination of the pluripotent genome," *Stem Cell Rev.*, 2:331-340, 2006.
Reijo Pera et al., "Gene expression profiles of human inner cell mass cells and embryonic stem cells," *Differentiation*, 78(1):18-23, 2009.
Ren et al., "Establishment of human embryonic stem cell line stably expressing Epstien-Barr virus-encoded nuclear antigen," *Acta Biochimica et Biophysica Sinica*, 37(1):68-73, 2005.
Reubinoff et al., "Embryonic stem cell lines from human blastocysts: somatic differentiation in vitro," *Nature Biotechnology*, 18:399-404, 2000.
Richards et al., "The transcriptome profile of human embryonic stem cells as defined by SAGE," *Stem Cells*, 22:51-64, 2004.
Silva et al., "Nanog promotes transfer of pluripotency after cell fusion," *Nature*, 441(7096):997-1001, 2006.
Taranger et al., "Induction of dedifferentiation, genomewide transcriptional programming, and epigenetic reprogramming by extracts of carcinoma and embryonic stem cells," *Mol. Biol. Cell.*, 16(12):5719-5735, 2005.
Third Declaration of Amanda Mack filed in the prosecution of U.S. Appl. No. 12/478,154, filed Jun. 28, 2013.
Vodyanik et al., "Human embryonic stem cell-derived $CD34^+$cells: efficient production in the coculture with OP9 stromal cells and analysis of lymphohematopoietic potential," *Blood*, 105(2):617-626, 2005.
Wade-Martins et al., "Long-term stability of large insert genomic DNA episomal shuttle vectors in human cells," *Nucleic Acids Research*, 27(7):1674-1682, 1999.
Woltejen et al., "piggyBAC transposition reprograms fibroblasts to induce pluripotent stem cells," *Nature*, 458(7239):766-770, 2009.
Yamanaka, "Strategies and new developments in the generation of patient-specific pluripotent stem cells," *Cell Stem Cell*, 1:39-49, 2007.
Yu et al., "Human embryonic stem cells reprogram myeloid precursors following cell-cell fusion,"*Stem Cells*, 24:168-176, 2006.
Zwaka et al., "Homologous recombination in human embryonic stem cells," *Nature Biotechnology*, 21(3):319-321, 2003.
Kameda et al., "A severe *de novo* methylation of episomal vectors by human ES cells," *Biochemical and Biophysical Research Communications*, 349:1269-1277, 2006.
Office Action issued in Japanese Application No. 2011-512634, dated Apr. 14, 2015.
Goessler et al., "Perspectives of gene therapy in stem cell tissue engineering," *Cells Tissues Organs*, 183(4):169-179, 2006.
Jackson et al., "Designing nonviral vectors for efficient gene transfer and long-term gene expression," *Molecular Therapy*, 14(5):613-626, 2006.
Liu et al., "Maintenance of pluripotency in human embryonic stem cells stably over-expressing enhanced green fluorescent protein," *Stem Cells Dev.*, 13(6):636-645, 2004.
Nishikawa, "Reprogramming by the numbers," *Nature Biotechnology*, 25(8):877-878, 2007.
Office Action issued in Australian Application No. 2009256202, mailed Apr. 29, 2014.
Office Action issued in Canadian Application No. 2,734,128, mailed May 5, 2014.

(56) References Cited

OTHER PUBLICATIONS

Polesskaya et al., "Lin-28 binds IGF-2 mRNA and participates in skeletal myogenesis by increasing translation efficiency," *Genes Dev.*, 21:1125-1138, 2007.
"pMX-STAT5A(1*6) Retroviral Vector," *Cell BioLabs, Inc.*, available at http://www.cellbiolabs.com, 2008.
Almqvist et al., "Functional interaction of Oct transcription factors with the family of repeats in Epstein-Barr virus oriP," *J. of General Virology*, 86 (Part 5): 1261-1267, 2005.
Altmann et al., "Transcriptional activation by EBV nuclear antigen 1 is essential for the expression of EBV's transforming genes," *PNAS*, 103(38):14188-14193, 2006.
Baer et al., "Transcriptional properties of genomic transgene integration sites marked by electroporation or retroviral infection," *Biochemistry*, 39:7041-7049, 2000.
Baker, "Reprogramming kinetics," *Nature Reports Stem Cells*, available at http://www.nature.com/stemcells/2008/0803/080306/full/stemcells.2008.44.html, published online Mar. 6, 2008.
Bingham, "Cosuppression comes to the animals," *Cell*, 90(3):385-387, 1997.
Bode et al., "The hitchhiking principle: Optimizing episomal vectors for the use in gene therapy and biotechnology," *Gene Ther. Mol. Biol.*, 6:33-46, 2001.
Bode et al., "The transgeneticist's toolbox: novel methods for the targeted modification of eukaryotic genomes," *Biol. Chem.*, 381:801-813, 2000.
Calos et al., "Stability without a centromere," *PNAS*, 95:4084-4085, 1998.
Garrick et al., "Repeat-induced gene silencing in mammals," *Nat. Genet.*, 18:56-59, 1998.
Hartenbach et al., "Autoregulated, bidirectional and multicistronic gas-inducible mammalian as well as lentiviral expression vectors," *Journal of Biotechnology*, 120:83-98, 2005.
Hung et al., "Maintenance of Epstein-Barr virus (EBV) oriP-based episomes requires EBV-encoded nuclear antigen-1 chromosome-binding domains, which can be replaced by high-mobility group-I or histone H1," *PNAS*, 98(4):1865-1870, 2001.
Jenke et al., "Nuclear scaffold/matrix attached region modules linked to a transcription unit are sufficient for replication and maintenance of a mammalian episome," *PNAS*, 101 (31), 11322-11327, 2004.
Kaufman et al., "Translational efficiency of polycistronic mRNAs and their utilization to express heterologous genes in mammalian cells," *The EMBO Journal*, 6:187-193, 1987.
Kennedy and Sugden, "EBNA-1, a bifunctional transcriptional activator," *Mol. And Cell. Biol.*, 23(19):6901-6908, 2003.
Kennedy et al., "Epstein-Barr virus provides a survival factor to Burkitt's lymphomas," *PNAS*, 100:14269-14274, 2003.
Leight and Sugden, "Establishment of an *ori*P replicon is dependent upon an infrequent, epigenetic event," *Mol. and Cell. Biol.*, 21(13):4149-4161, 2001.
Lindner and Sugden, "The plasmid replicon of Epstein-Barr virus: mechanistic insights into efficient licensed, extrachromosomal replication in human cells," *Plasmid*, 58 (1): 1-12, 2007.
Mackey and Sugden, "The linking regions of EBNA1 are essential for its support of replication and transcription," *Mol. Cell. Biol.*, 19(5):3349-3359, 1999.

Manzini et al., "Genetically modified pigs produced with a nonviral episomal vector," *PNAS*, 103(47):17672-17677, 2006.
Nanbo et al., "The coupling of synthesis and partitioning of EBV's plasmid replicon is revealed in live cells," *The EMBO Journal*, 26(19):4252-4562, 2007.
Office Action issued in European Application No. 09 759 392.5, mailed Jun. 1, 2011.
Office Action issued in European Application No. 09759392.5, mailed Sep. 5, 2014.
Office Action issued in European Application No. 09791378.4, mailed Oct. 14, 2014.
Office Action issued in Japanese Application No. 2011-512634, mailed Dec. 20, 2013, and English language translation thereof.
Office Action issued in Japanese Application No. 2011-523094, mailed Sep. 19, 2014 (English language translation).
Office Action issued in U.S. Appl. No. 12/478,154, mailed Dec. 29, 2010.
Office Action issued in U.S. Appl. No. 12/478,154, mailed Jul. 20, 2011.
Office Action issued in U.S. Appl. No. 12/478,154, mailed Mar. 29, 2011.
Office Action issued in U.S. Appl. No. 12/478,154, mailed May 2, 2013.
Office Action issued in U.S. Appl. No. 12/478,154, mailed Oct. 23, 2012.
PCT International Preliminary Report on Patentability, issued in International Application No. PCT/US2009/046209, dated Dec. 16, 2010.
PCT International Search Report and Written Opinion, issued in International Application No. PCT/US2009/046209, mailed Sep. 8, 2009.
Piechaczek et al., "A vector based on the SV40 origin of replication and chromosomal S/MARs replicates episomally in CHO cells," *Nucleic Acids Res.*, 27(2):426-428, 1999.
Schaarschmidt et al., "An episomal mammalian replicon: sequence-independent binding of the origin recognition complex," *EMBO J.*, 23(1):191-201, .2004.
Sears et al., "The amino terminus of Epstein-Barr Virus (EBV) nuclear antigen 1 contains AT hooks that facilitate the replication and partitioning of latent EBV genomes by tethering them to cellular chromosomes," *J. Virol.*, 78(21):11487-11505, 2004.
Stojkovic and Phinney, "Reprogramming battle: egg vs. virus," *Stem Cells Express*, available online at http://stemcells.alphamedpress.org/cgi/content/full/26/1/1 , Nov. 29, 2007.
Thomson et al., "Embryonic stem cell lines derived from human blastocysts," *Science*, 282:1145-1147, 1998.
Yates et al., "A cis-acting element from the Epstein-Barr viral genome that permits stable replication of recombinant plasmids in latently infected cells," *Proc. Natl. Acad. Sci. USA*, 81:3806-3810, 1984.
Yates et al., "Stable replication of plasmids derived from Epstein-Barr virus in various mammalian cells," *Nature*, 313:812-815, 1985.
Yu et al., "Human induced pluripotent stem cells free of vector and transgene sequences," *Science*, 324(5928):797-801, 2009.
Yu et al., Supporting Online Material for: "Induced pluripotent stem cell lines derived from human somatic cells," *Science*, available at http://www.sciencemag.org/cgi/data/1151526/DC1/2, Nov. 20, 2007.

* cited by examiner

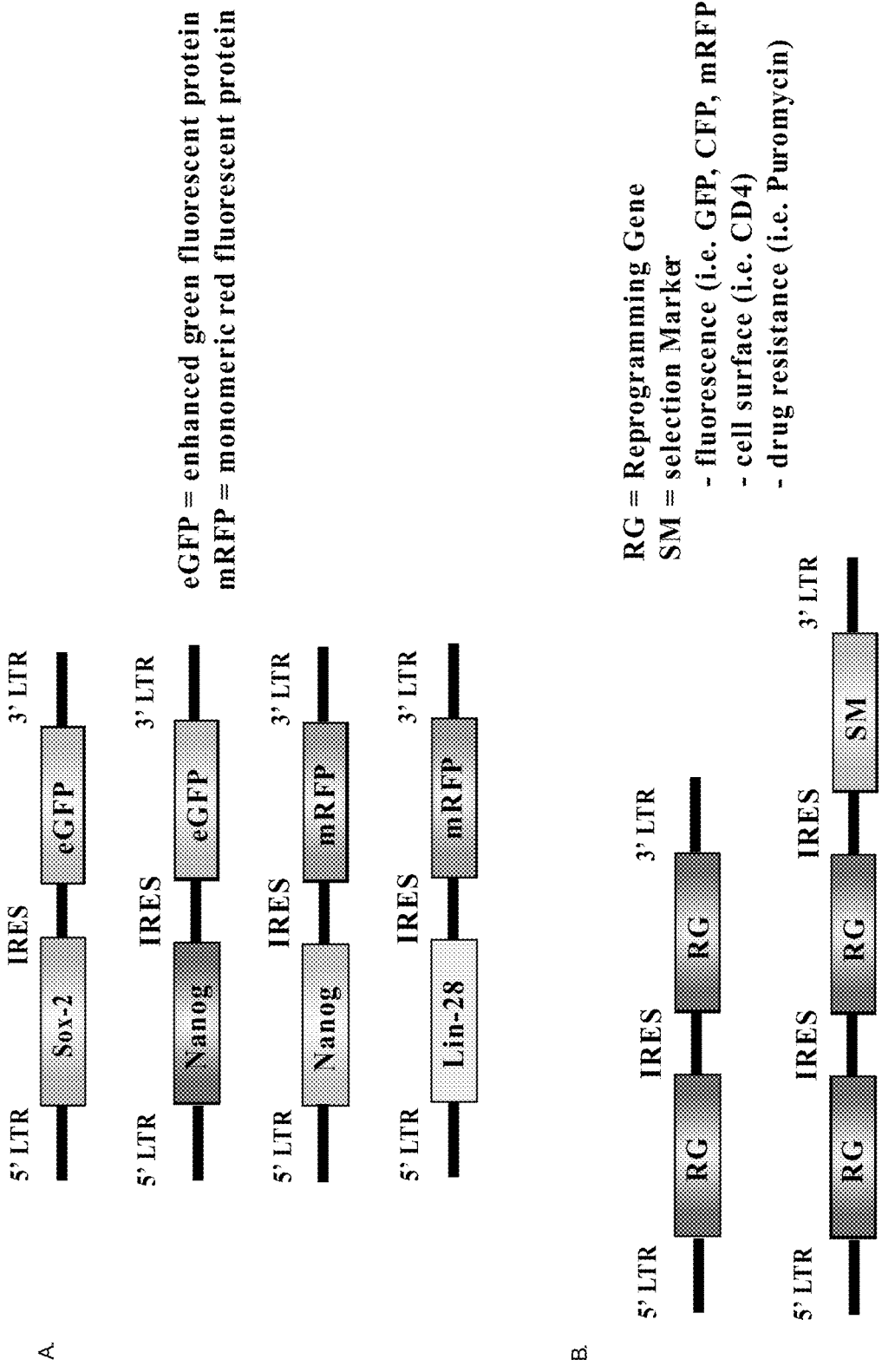

METHODS FOR THE PRODUCTION OF IPS CELLS

This application claims priority to U.S. Application No. 61/088,054 filed on Aug. 12, 2008, the entire disclosure of which is specifically incorporated herein by reference in its entirety without disclaimer.

BACKGROUND OF THE INVENTION

1. Field of the Invention

The present invention relates generally to the field of stem cells. More particularly, it concerns reprogramming of somatic cells.

2. Description of Related Art

In general, stem cells are undifferentiated cells which can give rise to a succession of mature functional cells. For example, a hematopoietic stem cell may give rise to any of the different types of terminally differentiated blood cells. Embryonic stem (ES) cells are derived from the embryo and are pluripotent, thus possessing the capability of developing into any organ or tissue type or, at least potentially, into a complete embryo.

Induced pluripotent stem cells, commonly abbreviated as iPS cells or iPSCs, are a type of pluripotent stem cells artificially derived from non-pluripotent cells, typically adult somatic cells, by inserting certain genes. Induced pluripotent stem cells are believed to be identical to natural pluripotent stem cells, such as embryonic stem cells in many respects, for example, in the expression of certain stem cell genes and proteins, chromatin methylation patterns, doubling time, embryoid body formation, teratoma formation, viable chimera formation, and potency and differentiability, but the full extent of their relation to natural pluripotent stem cells is still being assessed.

IPS cells were first produced in 2006 (Takahashi et al., 2006) from mouse cells and in 2007 from human cells (Takahashi et al., 2007; Yu et al, 2007). This has been cited as an important advancement in stem cell research, as it may allow researchers to obtain pluripotent stem cells, which are important in research and potentially have therapeutic uses, without the controversial use of embryos.

However, at this stage in the study of these induced pluripotent stem (iPS) cells, the efficiency of generating iPS cells is low, which hurdles the applicability of iPS cells in clinical studies. Therefore, there is a need to develop a method to enhance the efficiency of producing induced pluripotent stem cells.

SUMMARY OF THE INVENTION

The present invention overcomes a major deficiency in the art in providing induced pluripotent stem cells with improved efficiency. In a first embodiment there is provided a method for producing an induced pluripotent stem (iPS) cell population, the method comprising the steps of: (a) obtaining one or more reprogramming vectors, each of the vector comprising an expression cassette comprising: (i) a transcriptional regulatory element; (ii) a first nucleotide sequence operably linked to the transcriptional regulatory element, wherein the first nucleotide sequence encodes a reprogramming factor or a reporter; (iii) an IRES, which is located 3' to the first nucleotide sequence; and (iv) a second nucleotide sequence encoding a reprogramming factor or a reporter, located 3' to said IRES such that the second nucleotide sequence is under translational control of the IRES, wherein: (1) the second nucleotide sequence encodes another reprogramming factor or a reporter if the first nucleic acid encodes a reprogramming factor; and (2) the second nucleotide sequence encodes a reprogramming factor if the first nucleic acid encodes a reporter; (b) introducing the reprogramming vectors into cells of a population of somatic cells; (c) culturing the cells to expand the population; (d) selecting progeny cells of said expanded population, wherein said progeny has one or more characteristics of embryonic stem cells; and (e) culturing the selected progeny cells to provide the iPS cell population.

In certain aspects, the first nucleotide sequence encodes a reprogramming factor and the second nucleotide sequence encodes a reporter or vice versa, therefore simultaneous expression of reporter genes aids in the selection of reprogrammed cells as described below.

To coexpress multiple reprogramming factors under the same transcriptional regulatory element, the expression cassette may comprise a second IRES and a third nucleotide sequence located 3' to the second IRES such that the third nucleotide sequence is under translational control of the second IRES. In certain embodiments, the first and second nucleotide sequence may encode different reprogramming factors. In any of the above scenarios, a reporter may be encoded by the first, second or third nucleotide sequence for improving transfection and iPS cell selection efficiency.

The power of this invention partly relies on the expression of reporters, such as fluorescent proteins, which serve as indicators for infection efficiency, correlates generally with the levels of expression from the reprogramming genes on the same polycistronic transcript, and are silenced once cells have become fully induced to pluripotency. For example, the step c) of the above methods may further comprise selecting a population of somatic cells, wherein the somatic cells express the reporter, and culturing the selected cells to expand the population. Therefore, in certain aspects, it is possible to select cells that have been infected least to most efficiently based on the level of expression of the reporter, e.g., fluorescent protein using fluorescence-assisted cell sorting (FACs).

In exemplary embodiments, the reporter may be a cell surface marker, a fluorescent protein, an epitope, chloramphenicol acetyl transferase (CAT), luciferase or β-galactosidase. For instance, the fluorescent protein could be a green fluorescent protein (GFP), red fluorescent protein (RFP), blue fluorescent protein (BFP) or yellow fluorescent protein (YFP), or a variant thereof. Depending on the reporter used, the selection in the step c) may comprise fluorescence-activated cell sorting (FACS), CAT assay, luminescence assay or any methods known for an ordinary person in the art to detect or screen for reporter expression, in order to select for efficiently transfected cells. An alternative or complementary approach is to test the absence of exogenous reporter transcripts in progeny cells, using conventional methods, such as RT-PCR, in situ hybridization, RNA array, or hybridization (e.g., Northern blot).

In a further embodiment of the invention, the iPS reprogramming factors encoded by any of the nucleotide sequences comprised in the one or more reprogramming vectors may comprise at least one member from Sox family and at least one member from Oct family. Sox and Oct are thought to be central to the transcriptional regulatory hierarchy that specifies ES cell identity. For example, Sox may be Sox-1, Sox-2, Sox-3, Sox-15, or Sox-18; Oct may be Oct-4. Additional factors may increase the reprogramming efficiency, like Nanog, Lin28, Klf4, or c-Myc; specific sets of reprogramming factors may be a set comprising Sox-2, Oct-4, Nanog and, optionally, Lin-28; or comprising Sox-2, Oct4, Klf and, optionally, c-Myc. In a still further embodiment, the vector may be a viral vector, more specifically, a retroviral vector, such as murine leukemia virus (MLV), Moloney murine leukemia virus (MMLV), Akv-MLV, SL-3-3-MLV or another closely related virus. The viral vector could also be a lentiviral vector. In certain aspects, the transcriptional regulatory element may comprise a long terminal repeat region (LTR) to mediate integration of viral genes.

In certain embodiments, a polycistronic transcript may be used by employing one or more internal ribosome entry sites (IRESs). Exemplary IRES may be an encephalomyocarditis virus IRES, a picornavirus IRES, a foot-and-mouth disease virus IRES, a hepatitis A virus IRES, a hepatitis C virus IRES, a human rhinovirus IRES, a poliovirus IRES, a swine vesicular disease virus IRES, a turnip mosaic polyvirus IRES, a human fibroblast growth factor 2 mRNA IRES, a pestivirus IRES, a *Leishmania* RNA virus IRES, a Moloney murine leukemia virus IRES a human rhinovirus 14 IRES, an aphthovirus IRES, a human immunoglobulin heavy chain binding protein mRNA IRES, a *Drosophila* Antennapedia mRNA IRES, a human fibroblast growth factor 2 mRNA IRES, a hepatitis G virus IRES, a tobamovirus IRES, a vascular endothelial growth factor mRNA IRES, a Coxsackie B group virus IRES, a c-myc protooncogene mRNA IRES, a human MYT2 mRNA IRES, a human parechovirus type 1 virus IRES, a human parechovirus type 2 virus IRES, a eukaryotic initiation factor 4GI mRNA IRES, a *Plautia stali* intestine virus IRES, a Theiler's murine encephalomyelitis virus IRES, a bovine enterovirus IRES, a connexin 43 mRNA IRES, a homeodomain protein Gtx mRNA IRES, an AML1 transcription factor mRNA IRES, an NF-kappa B repressing factor mRNA IRES, an X-linked inhibitor of apoptosis mRNA IRES, a cricket paralysis virus RNA IRES, a p58 (PITSLRE) protein kinase mRNA IRES, an ornithine decarboxylase mRNA IRES, a connexin-32 mRNA IRES, a bovine viral diarrhea virus IRES, an insulin-like growth factor I receptor mRNA IRES, a human immunodeficiency virus type 1 gag gene IRES, a classical swine fever virus IRES, a Kaposi's sarcoma-associated herpes virus IRES, a short IRES selected from a library of random oligonucleotides, a Jembrana disease virus IRES, an apoptotic protease-activating factor 1 mRNA IRES, a *Rhopalosiphum padi* virus IRES, a cationic amino acid transporter mRNA IRES, a human insulin-like growth factor II leader 2 mRNA IRES, a giardiavirus IRES, a Smad5 mRNA IRES, a porcine teschovirus-1 talfan IRES, a *Drosophila* Hairless mRNA IRES, an hSNM1 mRNA IRES, a Cbfa1/Runx2 mRNA IRES, an Epstein-Barr virus IRES, a hibiscus chlorotic ringspot virus IRES, a rat pituitary vasopressin V1b receptor mRNA IRES, a human hsp70 mRNA IRES, or a variant thereof. In particular, the IRES element may be an encephalomyocarditis virus IRES.

In a further embodiment, the reprogramming vector may be introduced by liposome transfection, electroporation, particle bombardment, calcium phosphate, polycation, or polyanion, or any methods suitable for introducing exogenous genetics elements into the cells.

In still further aspects of the invention, the somatic cells may be from mammals, or more specifically, humans. The somatic cells may be terminally differentiated cells, or tissue stem cells, including, but not limited to, fibroblasts, hematopoietic cells, or mesenchymal cells. For example, the somatic cells are fibroblasts. The somatic cells may be from a tissue cell bank or from a selected human subject, specifically, a live human. Genomes from progeny of these somatic cells will be considered to be derived from these somatic cells of a certain source, such as a selected human individual.

In a certain aspect, the progeny cells could be selected for an essential loss of expression of the reporter, an undifferentiated morphology, an embryonic stem cell-specific marker or pluripotency or multi-lineage differentiation potential or any characteristics known in the art, or a combination thereof. This selection step may be employed at one or more time points after transfection to ensure that cells are in a pluripotent state and does not return to a differentiated state. Therefore, the selection step may be at a time after the progeny cells enter a self-sustaining pluripotent state, such as at least about 10 days to at least 30 days after the reprogramming vectors are introduced into cells.

Specifically, the progeny cells may be selected for an undifferentiated morphology because of its convenience. The embryonic stem cell-specific marker could be one or more specific markers selected from the group consisting of SSEA-3, SSEA-4, Tra-1-60 or Tra-1-81, Tra-2-49/6E, GDF3, REX1, FGF4, ESG1, DPPA2, DPPA4, and hTERT.

In a particular aspect, the progeny cells may be selected for iPS cells based on essentially no expression of introduced reporter genes because a reprogrammed cells is able to silence exogenously introduced material as a cell has become pluripotent. Therefore, an essential loss of reporter expression, e.g., fluorescence, is an indication in addition to morphological characteristics that cell have been reprogrammed. Such a characteristic may be selected by fluorescence-activated cell sorting (FACS), CAT assay or luminescence assay based on the reporter gene introduced. "Essentially loss" of reporter gene expression means that less than 1%, 0.5%, 0.1%, 0.05% or any intermediate percentage of cells of an iPS cell population comprises exogenous reporter expression.

In a further aspect, a reprogramming vector is also disclosed as comprising an expression cassette comprising: (a) a transcriptional regulatory element; (b) a first nucleotide sequence operably linked to the transcriptional regulatory element, wherein the first nucleotide sequence encodes a reprogramming factor or a reporter; c) an IRES, which is located 3' to the first nucleotide sequence; and (d) a second nucleotide sequence encoding a reprogramming factor or a reporter, located 3' to the IRES such that the second nucleotide sequence is under translational control of the IRES, wherein: (i) the second nucleotide sequence encodes another reprogramming factor or a reporter if the first nucleic acid encodes a reprogramming factor; and (ii) the second nucleotide sequence encodes a reprogramming factor if the first nucleic acid encodes a reporter.

In certain aspects, the first nucleotide sequence encodes a reprogramming factor and the second nucleotide sequence encodes a reporter or vice versa; alternatively, the first and second nucleotide sequences encode different reprogramming factors. To coexpress multiple reprogramming factors under the same transcriptional regulatory element, the expression cassette may comprise a second IRES and a third nucleotide sequence located 3' to the second IRES such that the third nucleotide sequence is under translational control of the second IRES. In any of the above scenarios, a reporter may be encoded by the first, second or third nucleotide sequence for improving transfection and iPS cell selection efficiency.

In a further aspect, there is also provided a reprogramming vector comprising a polycistronic expression cassette comprising: (a) a transcriptional regulatory element; and (b) a first and second coding sequence operably linked to the transcriptional regulatory element, wherein the first coding sequence encodes a reprogramming factor and the second coding sequence encodes a second reprogramming factor or a reporter. For example, the transcriptional regulatory element may comprise a long terminal repeat region, a promoter, an enhancer, a transcriptional control element, etc. As comprised in the polycistronic expression cassette, the second coding sequence may encode a reporter for facilitation of selection of expression or essential loss of expression of the coding sequence(s) to aid in the reprogramming process. Alternatively, the second coding sequence may be a second or more reprogramming factors to reduce proviral copies and chances for insertional mutagenesis by expressing two or more reprogramming factors from a single polycistronic transcript. Similarly, the polycistronic expression cassette may comprise one or more additional coding sequence (for example, a third, fourth, or fifth coding sequence, etc.) operably linked to the transcriptional regulatory element, wherein the one or more additional coding sequence encodes a reprogramming factor, a reporter, or a selection marker. For example, the selection marker may be an antibiotic resistance marker or a surface selection marker.

In exemplary embodiments of the reprogramming vector described above, the reporter may be a cell surface marker, a fluorescent protein, an epitope, chloramphenicol acetyl transferase (CAT), luciferase or β-galactosidase. For instance, the fluorescent protein could be a green fluorescent protein (GFP), red fluorescent protein (RFP), blue fluorescent protein (BFP) or yellow fluorescent protein (YFP), or a variant thereof, such as eGFP, eRFP, eBFP, eBFP2, eCFP, eYFP. In certain aspects, the reprogramming vector may further comprise a selection marker, such as an antibiotic resistance marker.

In a further embodiment of the reprogramming vector, the iPS reprogramming factor encoded by any of the nucleotide sequences comprised in the reprogramming vectors may comprise Sox, Oct, Nanog, Lin28, Klf4 or c-Myc. For example, Sox may be Sox-1, Sox-2, Sox-3, Sox-15, or Sox-18; Oct may be Oct-4. Additional factors may increase the reprogramming efficiency, like Nanog, Lin28, Klf4, or c-Myc. In a still further embodiment, the vector may be a viral vector, more specifically, a retroviral vector, such as murine leukemia virus (MLV), Moloney murine leukemia virus (MMLV), Akv-MLV, SL-3-3-MLV or another closely related virus. The viral vector could also be a lentiviral vector, an adenoviral vector, an Epstein-Barr Virus (EBV)-based vector. In certain aspects, the transcriptional regulatory element may comprise a long terminal repeat region (LTR) to mediate integration and transcription of exogenous genes.

In certain embodiments, the reprogramming vector may comprise one or more internal ribosome entry sites (IRESs) or any sequences sufficient to drive independent translation of coding sequences. Exemplary IRES may be an encephalomyocarditis virus IRES, a picornavirus IRES, a foot-and-mouth disease virus IRES, a hepatitis A virus IRES, a hepatitis C virus IRES, a human rhinovirus IRES, a poliovirus IRES, a swine vesicular disease virus IRES, a turnip mosaic polyvirus IRES, a human fibroblast growth factor 2 mRNA IRES, a pestivirus IRES, a *Leishmania* RNA virus IRES, a Moloney murine leukemia virus IRES a human rhinovirus 14 IRES, an aphthovirus IRES, a human immunoglobulin heavy chain binding protein mRNA IRES, a *Drosophila* Antennapedia mRNA IRES, a human fibroblast growth factor 2 mRNA IRES, a hepatitis G virus IRES, a tobamovirus IRES, a vascular endothelial growth factor mRNA IRES, a Coxsackie B group virus IRES, a c-myc protooncogene mRNA IRES, a human MYT2 mRNA IRES, a human parechovirus type 1 virus IRES, a human parechovirus type 2 virus IRES, a eukaryotic initiation factor 4GI mRNA IRES, a *Plautia stali* intestine virus IRES, a Theiler's murine encephalomyelitis virus IRES, a bovine enterovirus IRES, a connexin 43 mRNA IRES, a homeodomain protein Gtx mRNA IRES, an AML1 transcription factor mRNA IRES, an NF-kappa B repressing factor mRNA IRES, an X-linked inhibitor of apoptosis mRNA IRES, a cricket paralysis virus RNA IRES, a p58 (PITSLRE) protein kinase mRNA IRES, an ornithine decarboxylase mRNA IRES, a connexin-32 mRNA IRES, a bovine viral diarrhea virus IRES, an insulin-like growth factor I receptor mRNA IRES, a human immunodeficiency virus type 1 gag gene IRES, a classical swine fever virus IRES, a Kaposi's sarcoma-associated herpes virus IRES, a short IRES selected from a library of random oligonucleotides, a Jembrana disease virus IRES, an apoptotic protease-activating factor 1 mRNA IRES, a *Rhopalosiphum padi* virus IRES, a cationic amino acid transporter mRNA IRES, a human insulin-like growth factor II leader 2 mRNA IRES, a giardiavirus IRES, a Smad5 mRNA IRES, a porcine teschovirus-1 talfan IRES, a *Drosophila* Hairless mRNA IRES, an hSNM1 mRNA IRES, a Cbfa1/Runx2 mRNA IRES, an Epstein-Barr virus IRES, a hibiscus chlorotic ringspot virus IRES, a rat pituitary vasopressin V1b receptor mRNA IRES, a human hsp70 mRNA IRES, or a variant thereof. In particular, the IRES element may be an encephalomyocarditis virus IRES, a picornavirus IRES, or a foot-and-mouth disease virus IRES.

In further embodiments, there is provided a method for producing an induced pluripotent stem (iPS) cell population, the method comprising the steps of: (a) obtaining one or more reprogramming vectors described above; and (b) introducing the reprogramming vectors into cells of a population of somatic cells to provide an iPS cell population. In certain aspects, the one or more reprogramming vectors for producing iPS cells may include coding sequences that encode reprogramming factors comprising Sox and Oct.

The methods may further comprise the step of: (c) culturing the cells to expand the population; and (d) selecting progeny cells of the expanded population, wherein the progeny cells have one or more characteristics of embryonic stem cells. An additional step may be further comprised in the method: (e) culturing the selected progeny cells to provide the iPS cell population.

For the reprogramming vectors comprising coding sequence(s) encoding a reporter, the step (c) may further comprise selecting the population of somatic cells, wherein the selected somatic cells express the reporter because there is a correlation between the expression of the reporter and the reprogramming factor after introduction of the reprogramming vectors. The selecting in step c) may comprise an optical assay, fluorescence-activated cell sorting (FACS), CAT assay or luminescence assay for detection of reporter expression in certain aspects.

In certain aspects, the one or more reprogramming vector is introduced into the somatic cells by liposome transfection, electroporation, particle bombardment, calcium phosphate, polycation, polyanion, or any method known in the art for cellular entry of nucleotides.

For reprogramming, the somatic cells may be mammalian somatic cells, such as human somatic cells. The types of somatic cells could be fibroblasts, hematopoietic cells, lymphocytes (such as T cells or B cells), mesenchymal cells, islet cells, or tissue stem cells.

After a predetermined period for progeny cells to establish a self-sufficient pluripotent state, expression of the expression cassettes comprised in the viral vectors will be turned off. Therefore, the progeny cells could be selected for characteristics such as an essential loss of the reporter expression, or other known embryonic cell-like properties, such as an undifferentiated morphology, an embryonic stem cell-specific marker or pluripotency. The progeny cells could be selected by an optical assay, fluorescence-activated cell sorting (FACS), CAT assay or luminescence assay for selection of loss or reduction of reporter expression, or ES cell-specific surface markers, such as SSEA-3, SSEA-4, Tra-1-60 or Tra-1-81, Tra-2-49/6E, GDF3, REX1, FGF4, ESG1, DPPA2, DPPA4, and hTERT.

Embodiments discussed in the context of methods and/or compositions of the invention may be employed with respect to any other method or composition described herein. Thus, an embodiment pertaining to one method or composition may be applied to other methods and compositions of the invention as well.

As used herein the terms "encode" or "encoding" with reference to a nucleic acid are used to make the invention readily understandable by the skilled artisan however these terms may be used interchangeably with "comprise" or "comprising" respectively.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1: Examples of an IRES-dependent polycistronic system.

DESCRIPTION OF ILLUSTRATIVE EMBODIMENTS

I. The Present Invention

The ability to drive somatic, or fully differentiated, human cells back to a pluripotent or "stem cell" state would overcome many of the significant scientific and social challenges to the use of embryo-derived stem cells and help realize the promise of regenerative medicine. However, the current reprogramming process is inefficient and thus inhibits its application. The instant invention overcomes several major problems with current reprogramming technologies in generating induced pluripotent stem cells with improved efficiency. In contrast to previous methods generally using selection based on embryonic stem cell-like morphology alone, certain aspects of these methods use vectors expressing polycistronic transcripts encoding reporters in addition to reprogramming factors to refine selection and optimize the efficiency of reprogramming cells. Further embodiments and advantages of the invention are described below.

II. Definitions

"Reprogramming" is a process that confers on a cell a measurably increased capacity to form progeny of at least one new cell type, either in culture or in vivo, than it would have under the same conditions without reprogramming. More specifically, reprogramming is a process that confers on a somatic cell a pluripotent potential. This means that after sufficient proliferation, a measurable proportion of progeny having phenotypic characteristics of the new cell type if essentially no such progeny could form before reprogramming; otherwise, the proportion having characteristics of the new cell type is measurably more than before reprogramming. Under certain conditions, the proportion of progeny with characteristics of the new cell type may be at least about 1%, 5%, 25% or more in the in order of increasing preference.

A "vector" or "construct" (sometimes referred to as gene delivery or gene transfer "vehicle") refers to a macromolecule or complex of molecules comprising a polynucleotide to be delivered to a host cell, either in vitro or in vivo.

By "expression construct" or "expression cassette" is meant a nucleic acid molecule that is capable of directing transcription. An expression construct includes, at the least, a promoter or a structure functionally equivalent to a promoter. Additional elements, such as an enhancer, and/or a transcription termination signal, may also be included.

The term "exogenous," when used in relation to a protein, gene, nucleic acid, or polynucleotide in a cell or organism refers to a protein, gene, nucleic acid, or polynucleotide which has been introduced into the cell or organism by artificial or natural means, or in relation to a cell refers to a cell which was isolated and subsequently introduced to other cells or to an organism by artificial or natural means. An exogenous nucleic acid may be from a different organism or cell, or it may be one or more additional copies of a nucleic acid which occurs naturally within the organism or cell. An exogenous cell may be from a different organism, or it may be from the same organism. By way of a non-limiting example, an exogenous nucleic acid is in a chromosomal location different from that of natural cells, or is otherwise flanked by a different nucleic acid sequence than that found in nature.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

A "gene," "polynucleotide," "coding region," "sequence," "segment," "fragment," or "transgene" which "encodes" a particular protein, is a nucleic acid molecule which is transcribed and optionally also translated into a gene product, e.g., a polypeptide, in vitro or in vivo when placed under the control of appropriate regulatory sequences. The coding region may be present in either a cDNA, genomic DNA, or RNA form. When present in a DNA form, the nucleic acid molecule may be single-stranded (i.e., the sense strand) or double-stranded. The boundaries of a coding region are determined by a start codon at the 5' (amino) terminus and a translation stop codon at the 3' (carboxy) terminus. A gene can include, but is not limited to, cDNA from prokaryotic or eukaryotic mRNA, genomic DNA sequences from prokaryotic or eukaryotic DNA, and synthetic DNA sequences. A transcription termination sequence will usually be located 3' to the gene sequence.

The term "control elements" refers collectively to promoter regions, polyadenylation signals, transcription termination sequences, upstream regulatory domains, origins of replication, internal ribosome entry sites ("IRES"), enhancers, splice junctions, and the like, which collectively provide for the replication, transcription, post-transcriptional processing and translation of a coding sequence in a recipient cell. Not all of these control elements need always be present so long as the selected coding sequence is capable of being replicated, transcribed and translated in an appropriate host cell.

The term "LTR" as used herein refers to the long terminal repeat found at each end of a provirus (e.g., the integrated form of a retrovirus). The LTR contains numerous regulatory signals including transcriptional control elements, polyadenylation signals and sequences needed for replication and integration of the viral genome. The viral LTR is divided into three regions called U3, R and U5. The U3 region contains the enhancer and promoter elements. The U5 region contains the polyadenylation signals. The R (repeat) region separates the U3 and U5 regions and transcribed sequences of the R region appear at both the 5' and 3' ends of the viral RNA.

"Fluorescent protein" refers to a class of proteins comprising a fluorescent chromophore, the chromophore being formed from at least 3 amino acids and characterized by a cyclization reaction creating a p-hydroxybenzylidene-imidazolidinone chromophore. The chromophore does not contain a prosthetic group and is capable of emitting light of selective energy, the energy having been stored in the chromophore by previous illumination from an outside light source comprising the correct wavelength(s). Spontaneously fluorescent proteins can be of any structure, with a chromophore comprising any number of amino acids, provided that the chromophore comprises the p-hydroxybenzylidene-imidazolidinone ring structure, as detailed above. SFP's typically, but not exclusively, comprise a β-barrel structure such as that found in green fluorescent proteins and described in Chalfie et al. (1994).

Fluorescent proteins characteristically exhibit "fluorescent properties," which are the ability to produce, in response to an incident light of a particular wavelength absorbed by the protein, a light of longer wavelength.

The term "promoter" is used herein in its ordinary sense to refer to a nucleotide region comprising a DNA regulatory sequence, wherein the regulatory sequence is derived from a gene which is capable of binding RNA polymerase and initiating transcription of a downstream (3' direction) coding sequence.

By "enhancer" is meant a nucleic acid sequence that, when positioned proximate to a promoter, confers increased transcription activity relative to the transcription activity resulting from the promoter in the absence of the enhancer domain.

By "operably linked" with reference to nucleic acid molecules is meant that two or more nucleic acid molecules (e.g., a nucleic acid molecule to be transcribed, a promoter, and an enhancer element) are connected in such a way as to permit transcription of the nucleic acid molecule. "Operably linked" with reference to peptide and/or polypeptide molecules is meant that two or more peptide and/or polypeptide molecules are connected in such a way as to yield a single polypeptide chain, i.e., a fusion polypeptide, having at least one property of each peptide and/or polypeptide component of the fusion. The fusion polypeptide is preferably chimeric, i.e., composed of heterologous molecules.

The term "cell" is herein used in its broadest sense in the art and refers to a living body which is a structural unit of tissue of a multicellular organism, is surrounded by a membrane structure which isolates it from the outside, has the capability of self replicating, and has genetic information and a mechanism for expressing it. Cells used herein may be naturally-occurring cells or artificially modified cells (e.g., fusion cells, genetically modified cells, etc.).

As used herein, the term "stem cell" refers to a cell capable of self replication and pluripotency. Typically, stem cells can regenerate an injured tissue. Stem cells herein may be, but are not limited to, embryonic stem (ES) cells or tissue stem cells (also called tissue-specific stem cell, or somatic stem cell). Any artificially produced cell which can have the above-described abilities (e.g., fusion cells, reprogrammed cells, or the like used herein) may be a stem cell.

"Embryonic stem (ES) cells" are pluripotent stem cells derived from early embryos. An ES cell was first established in 1981, which has also been applied to production of knock-out mice since 1989. In 1998, a human ES cell was established, which is currently becoming available for regenerative medicine.

Unlike ES cells, tissue stem cells have a limited differentiation potential. Tissue stem cells are present at particular locations in tissues and have an undifferentiated intracellular structure. Therefore, the pluripotency of tissue stem cells is typically low. Tissue stem cells have a higher nucleus/cytoplasm ratio and have few intracellular organelles. Most tissue stem cells have low pluripotency, a long cell cycle, and proliferative ability beyond the life of the individual. Tissue stem cells are separated into categories, based on the sites from which the cells are derived, such as the dermal system, the digestive system, the bone marrow system, the nervous system, and the like. Tissue stem cells in the dermal system include epidermal stem cells, hair follicle stem cells, and the like. Tissue stem cells in the digestive system include pancreatic (common) stem cells, liver stem cells, and the like. Tissue stem cells in the bone marrow system include hematopoietic stem cells, mesenchymal stem cells, and the like. Tissue stem cells in the nervous system include neural stem cells, retinal stem cells, and the like.

"Induced pluripotent stem cells," commonly abbreviated as iPS cells or iPSCs, refer to a type of pluripotent stem cell artificially prepared from a non-pluripotent cell, typically an adult somatic cell, or terminally differentiated cell, such as fibroblast, a hematopoietic cell, a myocyte, a neuron, an epidermal cell, or the like, by inserting certain genes, referred to as reprogramming factors.

"Pluripotency" refers to a stem cell that has the potential to differentiate into all cells constituting one or more tissues or organs, or preferably, any of the three germ layers: endoderm (interior stomach lining, gastrointestinal tract, the lungs), mesoderm (muscle, bone, blood, urogenital), or ectoderm (epidermal tissues and nervous system). "Pluripotent stem cells" used herein refer to cells that can differentiate into cells derived from any of the three germ layers, for example, descendants of totipotent cells or induced pluripotent cells.

"Self-renewal" refers to the ability to go through numerous cycles of cell division while maintaining the undifferentiated state.

As used herein, the term "somatic cell" refers to any cell other than germ cells, such as an egg, a sperm, or the like, which does not directly transfer its DNA to the next generation. Typically, somatic cells have limited or no pluripotency. Somatic cells used herein may be naturally-occurring or genetically modified.

III. General Background for Induced Pluripotent Stem Cells

In certain embodiments of the invention, there are disclosed methods of reprogramming somatic cells with a reprogramming vector expressing a polycistronic transcript encoding both reporters and reprogramming factors. For example, these cells could be first selected for expression of reporter genes to enrich transformed cells and later their progeny selected for silencing of reporter genes for induced pluripotent stem cells. Understanding of embryonic stem cell characteristics could help select induced pluripotent stem cells in addition to these methods. Reprogramming factors known from stem cell reprogramming studies could be used for these novel methods. It is further contemplated that these induced pluripotent stem cells could be potentially used to replace embryonic stem cells for therapeutics and research applications due to the ethics hurdle to use the latter.

A. Stem Cells

Stem cells are cells found in most, if not all, multi-cellular organisms. They are characterized by the ability to renew themselves through mitotic cell division and differentiating into a diverse range of specialized cell types. The two broad types of mammalian stem cells are: embryonic stem cells that are found in blastocysts, and adult stem cells that are found in adult tissues. In a developing embryo, stem cells can differentiate into all of the specialized embryonic tissues. In adult organisms, stem cells and progenitor cells act as a repair system for the body, replenishing specialized cells, but also maintain the normal turnover of regenerative organs, such as blood, skin or intestinal tissues.

As stem cells can be grown and transformed into specialized cells with characteristics consistent with cells of various tissues such as muscles or nerves through cell culture, their use in medical therapies has been proposed. In particular, embryonic cell lines, autologous embryonic stem cells generated through therapeutic cloning, and highly plastic adult stem cells from the umbilical cord blood or bone marrow are touted as promising candidates. Most recently, the reprogramming of adult cells into induced pluripotent stem cells has enormous potential for replacing embryonic stem cells.

B. Embryonic Stem Cells

Embryonic stem cell lines (ES cell lines) are cultures of cells derived from the epiblast tissue of the inner cell mass (ICM) of a blastocyst or earlier morula stage embryos. A blastocyst is an early stage embryo-approximately four to five days old in humans and consisting of 50-150 cells. ES cells are pluripotent and give rise during development to all derivatives of the three primary germ layers: ectoderm, endoderm and mesoderm. In other words, they can develop into each of the more than 200 cell types of the adult body when given sufficient and necessary stimulation for a specific cell type. They do not contribute to the extraembryonic membranes or the placenta.

Nearly all research to date has taken place using mouse embryonic stem cells (mES) or human embryonic stem cells (hES). Both have the essential stem cell characteristics, yet they require very different environments in order to maintain an undifferentiated state. Mouse ES cells may be grown on a layer of gelatin and require the presence of Leukemia Inhibitory Factor (LIF). Human ES cells could be grown on a feeder layer of mouse embryonic fibroblasts (MEFs) and often require the presence of basic Fibroblast Growth Factor (bFGF or FGF-2). Without optimal culture conditions or genetic manipulation (Chambers et al., 2003), embryonic stem cells will rapidly differentiate.

A human embryonic stem cell may be also defined by the presence of several transcription factors and cell surface proteins. The transcription factors Oct-4, Nanog, and Sox2 form the core regulatory network that ensures the suppression of genes that lead to differentiation and the maintenance of pluripotency (Boyer et al., 2005). The cell surface antigens most commonly used to identify hES cells include the glycolipids SSEA3 and SSEA4 and the keratan sulfate antigens Tra-1-60 and Tra-1-81.

After twenty years of research, there are no approved treatments or human trials using embryonic stem cells. ES cells, being pluripotent cells, require specific signals for correct differentiation—if injected directly into the body, ES cells will differentiate into many different types of cells, causing a teratoma. Differentiating ES cells into usable cells while avoiding transplant rejection are just a few of the hurdles that embryonic stem cell researchers still face. Many nations currently have moratoria on either ES cell research or the production of new ES cell lines. Because of their combined abilities of unlimited expansion and pluripotency, embryonic stem cells remain a theoretically potential source for regenerative medicine and tissue replacement after injury or disease. However, one way to circumvent these issues is to induce pluripotent status in somatic cells by direct reprogramming.

C. Reprogramming Factors

The generation of iPS cells is crucial on the genes used for the induction. The following factors or combination thereof could be used in the vector system disclosed in the present invention. In certain aspects, nucleic acids encoding Sox and Oct (preferably Oct3/4) will be included into the reprogramming vector. For example, a reprogramming vector may comprise expression cassettes encoding Sox2, Oct4, Nanog and optionally Lin-28, or expression cassettes encoding Sox2, Oct4, Klf4 and optionally c-myc. Nucleic acids encoding these reprogramming factors may be comprised in the same expression cassette, different expression cassettes, the same reprogramming vector, or different reprogramming vectors.

Oct-3/4 and certain members of the Sox gene family (Sox1, Sox2, Sox3, and Sox15) have been identified as crucial transcriptional regulators involved in the induction process whose absence makes induction impossible. Additional genes, however, including certain members of the Klf family (Klf1, Klf2, Klf4, and Klf5), the Myc family (C-myc, L-myc, and N-myc), Nanog, and LIN28, have been identified to increase the induction efficiency. Oct-3/4 (Pou5f1) is one of the family of octamer ("Oct") transcription factors, and plays a crucial role in maintaining pluripotency. The absence of Oct-3/4 in Oct-3/4+ cells, such as blastomeres and embryonic stem cells, leads to spontaneous trophoblast differentiation, and presence of Oct-3/4 thus gives rise to the pluripotency and differentiation potential of embryonic stem cells. Various other genes in the "Oct" family, including Oct-3/4's close relatives, Oct1 and Oct6, fail to elicit induction, thus demonstrating the exclusiveness of Oct-3/4 to the induction process.

The Sox family of genes is associated with maintaining pluripotency similar to Oct-3/4, although it is associated with multipotent and unipotent stem cells in contrast with Oct-3/4, which is exclusively expressed in pluripotent stem cells. While Sox2 was the initial gene used for induction by Yamanaka et al. (2007), Jaenisch et al. (1988) and Yu et al. (2007), other genes in the Sox family have been found to work as well in the induction process. Sox1 yields iPS cells with a similar efficiency as Sox2, and genes Sox3, Sox15, and Sox18 also generate iPS cells, although with decreased efficiency.

In embryonic stem cells, at least an Oct member such as Oct-3/4 and at least a Sox member such as Sox2, are necessary in promoting pluripotency. Yamanaka et al. (2007) reported that Nanog was unnecessary for induction although Yu et al. (2007) has reported it is possible to generate iPS cells with Nanog as one of the factors and Nanog certainly enhances reprogramming efficiency dose-dependently.

LIN28 is an mRNA binding protein expressed in embryonic stem cells and embryonic carcinoma cells associated with differentiation and proliferation. Yu et al. (2007) demonstrated it is a factor in iPS generation, although it is unnecessary.

Klf4 of the Klf family of genes was initially identified by Yamanaka et al. and confirmed by Jaenisch et al. (1988) as a factor for the generation of mouse iPS cells and was demonstrated by Yamanaka et al. (2007) as a factor for generation of human iPS cells. However, Thompson et al. reported that Klf4 was unnecessary for generation of human iPS cells and in fact failed to generate human iPS cells. Klf2 and Klf4 were found to be factors capable of generating iPS cells, and related genes Klf1 and Klf5 did as well, although with reduced efficiency.

The Myc family of genes are proto-oncogenes implicated in cancer. Yamanaka et al. and Jaenisch et al. (1988) demonstrated that c-myc is a factor implicated in the generation of mouse iPS cells and Yamanaka et al. demonstrated it was a factor implicated in the generation of human iPS cells. However, Thomson et al. and Yamanaka et al. (2007) reported that c-myc was unnecessary for generation of human iPS cells. Usage of the "myc" family of genes in induction of iPS cells is troubling for the eventuality of iPS cells as clinical therapies, as 25% of mice transplanted with c-myc-induced iPS cells developed lethal teratomas. N-myc and L-myc have been identified to induce in the stead of c-myc with similar efficiency.

D. Induction of Pluripotent Stem Cells Using Reprogramming Factors

IPS cells are typically derived by transfection of certain stem cell-associated genes into non-pluripotent cells, such as adult fibroblasts. Transfection is typically achieved through integrating viral vectors in the current practice, such as retroviruses. Transfected genes include the master transcriptional regulators Oct-3/4 (Pouf51) and Sox2, although it is suggested that other genes enhance the efficiency of induction. After a critical period, small numbers of transfected cells begin to become morphologically and biochemically similar to pluripotent stem cells, and are typically isolated through morphological selection, doubling time, or through a reporter gene and antibiotic infection.

In November 2007, a milestone was achieved by creating iPS from adult human cells from two independent research teams' studies (Yu et al., 2007; Yamanaka et al., 2007). With the same principle used earlier in mouse models, Yamanaka had successfully transformed human fibroblasts into pluripotent stem cells using the same four pivotal genes: Oct3/4, Sox2, Klf4, and c-Myc with a retroviral system but c-Myc is oncogenic. Thomson and colleagues used Oct4, Sox2, NANOG, and a different gene LIN28 using a lentiviral system avoiding the use of c-Myc.

However, current process for generation of induce pluripotent stem cells is slow and inefficient, with most cells failing. To improve the efficiency of this process, in certain aspects, the present methods and vectors utilize a polycistronic construct containing a reprogramming factor and a reporter to optimize transfection efficiency by selecting for the presence of reporters and later improve selection of pluripotent cells by selecting against reporter gene expression because transgene silencing is very effective in pluripotent cells.

IV. Polycistronic System for Generating Induced Pluripotent Stem Cells

In certain aspects of the present invention, the flexibility and efficient expression from this IRES-dependent polycistronic system underlie its advantages and establish it as a useful tool to enhance the efficiency of producing iPS cells. The various permutations of this system include but are not limited to (see FIG. 1 for examples): 1) altering the reporters used (e.g., cyan fluorescent protein, red fluorescent protein, etc), 2) substituting the reporter gene for another reprogramming gene so that fewer viruses need to be synthesized, or 3) creating a cassette with two IRES' such that the LTR would drive expression of Oct4 IRES Sox-2 IRES eGFP.

A. Internal Ribosome Entry Sites (IRES)

IRES sequences are included in the present invention to allow polycistronic transcripts to be produced. This allows expression systems of the present invention to produce multiple reprogramming factors from a single transcriptional unit, or to readily incorporate reporters into polycistronic transcripts without creating fusion proteins or the necessity of additional regulatory elements to control expression of additional genes.

Most eukaryotic and viral messages initiate translation by a mechanism involving recognition of a 7-methylguanosine cap at the 5' end of the mRNA. In a few cases, however, translation occurs via a cap-independent mechanism in which an internal ribosome entry site (IRES) positioned 3' downstream of the gene translated from the cap region of the mRNA is recognized by the ribosome, allowing translation of a second coding region from the transcript. Therefore, IRES elements are able to bypass the ribosome scanning model of 5' methylated Cap dependent translation and begin translation at internal sites (Pelletier and Sonenberg, 1988).

This is particularly important in the present invention as an IRES sequence allows simultaneous expression of multiple proteins from a single genetic locus. IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

A particularly preferred embodiment involves including coding sequences for both a desired recombinant product and a reporter within the same polycistronic transcript. Successful transformation events are marked by both expression of the desired reprogramming factors and the easily detectable reporters, facilitating selection of successfully transfected cells.

IRES elements from two members of the picornavirus family (polio and encephalomyocarditis) have been described (Pelletier and Sonenberg, 1988), as well an IRES from a mammalian message (Macejak and Sarnow, 1991). Certain examples include those IRES elements from poliovirus Type I, the 5'UTR of encephalomyocarditis virus (EMV), of "Thelier's murine encephalomyelitis virus (TMEV), of "foot and mouth disease virus" (FMDV), of "bovine enterovirus (BEV), of "coxsackie B virus" (CBV), or of "human rhinovirus" (HRV), or the "human immunoglobulin heavy chain binding protein" (BIP) 5'UTR, the *Drosophila* antennapediae 5'UTR or the *Drosophila* ultrabithorax 5'UTR, or genetic hybrids or fragments from the above-listed sequences. IRES sequences are described in Kim et al. (1992) and McBratney et al. (1993).

B. Reporters

Certain embodiments of the present invention utilize reporter genes to indicate successful transformation. For example, the reporter gene can be located within expression cassettes and under the control of the regulatory elements normally associated with the coding region of a reprogramming gene for simultaneous expression. A reporter allows the cells containing the reprogramming vector to be isolated without placing them under drug or other selective pressures or otherwise risking cell viability. An additional advantage is to enrich induced pluripotent stem cells with silenced reporter expression.

Examples of such reporters include genes encoding cell surface proteins (e.g., CD4, HA epitope), fluorescent proteins, antigenic determinants and enzymes (e.g., β-galactosidase). The vector containing cells may be isolated, e.g., by FACS using fluorescently-tagged antibodies to the cell surface protein or substrates that can be converted to fluorescent products by a vector encoded enzyme.

In specific embodiments, the reporter gene is a fluorescent protein. A broad range of fluorescent protein genetic variants have been developed that feature fluorescence emission spectral profiles spanning almost the entire visible light spectrum (see Table 1 for non-limiting examples). Mutagenesis efforts in the original *Aequorea victoria* jellyfish green fluorescent protein have resulted in new fluorescent probes that range in color from blue to yellow, and are some of the most widely used in vivo reporter molecules in biological research. Longer wavelength fluorescent proteins, emitting in the orange and red spectral regions, have been developed from the marine anemone, *Discosoma striata*, and reef corals belonging to the class Anthozoa. Still other species have been mined to produce similar proteins having cyan, green, yellow, orange, and deep red fluorescence emission. Developmental research efforts are ongoing to improve the brightness and stability of fluorescent proteins, thus improving their overall usefulness.

TABLE 1

Fluorescent Protein Properties

| Protein (Acronym) | Excitation Maximum (nm) | Emission Maximum (nm) | Molar Extinction Coefficient | Quantum Yield | in vivo Structure | Relative Brightness (% of EGFP) |
|---|---|---|---|---|---|---|
| GFP (wt) | 395/475 | 509 | 21,000 | 0.77 | Monomer* | 48 |
| Green Fluorescent Proteins | | | | | | |
| EGFP | 484 | 507 | 56,000 | 0.60 | Monomer* | 100 |
| AcGFP | 480 | 505 | 50,000 | 0.55 | Monomer* | 82 |
| TurboGFP | 482 | 502 | 70,000 | 0.53 | Monomer* | 110 |
| Emerald | 487 | 509 | 57,500 | 0.68 | Monomer* | 116 |
| Azami Green | 492 | 505 | 55,000 | 0.74 | Monomer | 121 |
| ZsGreen | 493 | 505 | 43,000 | 0.91 | Tetramer | 117 |
| Blue Fluorescent Proteins | | | | | | |
| EBFP | 383 | 445 | 29,000 | 0.31 | Monomer* | 27 |
| Sapphire | 399 | 511 | 29,000 | 0.64 | Monomer* | 55 |
| T-Sapphire | 399 | 511 | 44,000 | 0.60 | Monomer* | 79 |
| Cyan Fluorescent Proteins | | | | | | |
| ECFP | 439 | 476 | 32,500 | 0.40 | Monomer* | 39 |
| mCFP | 433 | 475 | 32,500 | 0.40 | Monomer | 39 |
| Cerulean | 433 | 475 | 43,000 | 0.62 | Monomer* | 79 |
| CyPet | 435 | 477 | 35,000 | 0.51 | Monomer* | 53 |
| AmCyan1 | 458 | 489 | 44,000 | 0.24 | Tetramer | 31 |
| Midori-Ishi Cyan | 472 | 495 | 27,300 | 0.90 | Dimer | 73 |
| mTFP1 (Teal) | 462 | 492 | 64,000 | 0.85 | Monomer | 162 |
| Yellow Fluorescent Proteins | | | | | | |
| EYFP | 514 | 527 | 83,400 | 0.61 | Monomer* | 151 |
| Topaz | 514 | 527 | 94,500 | 0.60 | Monomer* | 169 |
| Venus | 515 | 528 | 92,200 | 0.57 | Monomer* | 156 |
| mCitrine | 516 | 529 | 77,000 | 0.76 | Monomer | 174 |
| YPet | 517 | 530 | 104,000 | 0.77 | Monomer* | 238 |
| PhiYFP | 525 | 537 | 124,000 | 0.39 | Monomer* | 144 |
| ZsYellow1 | 529 | 539 | 20,200 | 0.42 | Tetramer | 25 |
| mBanana | 540 | 553 | 6,000 | 0.7 | Monomer | 13 |
| Orange and Red Fluorescent Proteins | | | | | | |
| Kusabira Orange | 548 | 559 | 51,600 | 0.60 | Monomer | 92 |
| mOrange | 548 | 562 | 71,000 | 0.69 | Monomer | 146 |
| dTomato | 554 | 581 | 69,000 | 0.69 | Dimer | 142 |
| dTomato-Tandem | 554 | 581 | 138,000 | 0.69 | Monomer | 283 |
| DsRed | 558 | 583 | 75,000 | 0.79 | Tetramer | 176 |
| DsRed2 | 563 | 582 | 43,800 | 0.55 | Tetramer | 72 |

TABLE 1-continued

Fluorescent Protein Properties

| Protein (Acronym) | Excitation Maximum (nm) | Emission Maximum (nm) | Molar Extinction Coefficient | Quantum Yield | in vivo Structure | Relative Brightness (% of EGFP) |
|---|---|---|---|---|---|---|
| DsRed-Express (T1) | 555 | 584 | 38,000 | 0.51 | Tetramer | 58 |
| DsRed-Monomer | 556 | 586 | 35,000 | 0.10 | Monomer | 10 |
| mTangerine | 568 | 585 | 38,000 | 0.30 | Monomer | 34 |
| mStrawberry | 574 | 596 | 90,000 | 0.29 | Monomer | 78 |
| AsRed2 | 576 | 592 | 56,200 | 0.05 | Tetramer | 8 |
| mRFP1 | 584 | 607 | 50,000 | 0.25 | Monomer | 37 |
| JRed | 584 | 610 | 44,000 | 0.20 | Dimer | 26 |
| mCherry | 587 | 610 | 72,000 | 0.22 | Monomer | 47 |
| HcRed1 | 588 | 618 | 20,000 | 0.015 | Dimer | 1 |
| mRaspberry | 598 | 625 | 86,000 | 0.15 | Monomer | 38 |
| HcRed-Tandem | 590 | 637 | 160,000 | 0.04 | Monomer | 19 |
| mPlum | 590 | 649 | 41,000 | 0.10 | Monomer | 12 |
| AQ143 | 595 | 655 | 90,000 | 0.04 | Tetramer | 11 |

*Weak Dimer

V. Vector Construction and Delivery

In certain embodiments, reprogramming vectors could be viral vectors, for example, retroviral vectors or lentiviral vectors to express these reprogramming factors in cells. The novel features of these methods are use of polycistronic transcripts as described above, which will facilitate selection of transformed cells and induced pluripotent cells. Details of construction of these vectors and delivery methods are disclosed below.

A. Vector

One of skill in the art would be well equipped to construct a vector through standard recombinant techniques (see, for example, Sambrook et al., 2001 and Ausubel et al., 1996, both incorporated herein by reference). Vectors include but are not limited to, plasmids, cosmids, viruses (bacteriophage, animal viruses, and plant viruses), and artificial chromosomes (e.g., YACs), such as retroviral vectors (e.g. derived from Moloney murine leukemia virus vectors (MoMLV), MSCV, SFFV, MPSV, SNV etc), lentiviral vectors (e.g. derived from HIV-1, HIV-2, SIV, BIV, FIV etc.), adenoviral (Ad) vectors including replication competent, replication deficient and gutless forms thereof, adeno-associated viral (AAV) vectors, simian virus 40 (SV-40) vectors, bovine papilloma virus vectors, Epstein-Barr virus, herpes virus vectors, vaccinia virus vectors, Harvey murine sarcoma virus vectors, murine mammary tumor virus vectors, Rous sarcoma virus vectors.

In one preferred approach, the vector is a viral vector. In particular, retroviral and lentiviral vectors have been successfully used in reprogramming somatic cells. Viral vectors can efficiently transduce cells and introduce their own DNA into a host cell. In generating recombinant viral vectors, non-essential genes are typically replaced with a gene or coding sequence for a heterologous (or non-native) protein.

Viral vectors are a kind of expression construct that utilizes viral sequences to introduce nucleic acid and possibly proteins into a cell. The ability of certain viruses to infect cells or enter cells via receptor-mediated endocytosis, and to integrate into host cell genome and express viral genes stably and efficiently have made them attractive candidates for the transfer of foreign nucleic acids into cells (e.g., mammalian cells). Non-limiting examples of virus vectors that may be used to deliver a polycistronic transcript of the present invention are described below.

a. Retroviral Vectors

Retroviruses have promise as gene delivery vectors due to their ability to integrate their genes into the host genome, transferring a large amount of foreign genetic material, infecting a broad spectrum of species and cell types and of being packaged in special cell-lines (Miller, 1992).

In order to construct a retroviral vector, a nucleic acid is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into a special cell line (e.g., by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

b. Lentiviral Vectors

Lentiviruses are complex retroviruses, which, in addition to the common retroviral genes gag, pol, and env, contain other genes with regulatory or structural function. Lentiviral vectors are well known in the art (see, for example, Naldini et al., 1996; Zufferey et al., 1997; Blomer et al., 1997; U.S. Pat. Nos. 6,013,516 and 5,994,136).

Recombinant lentiviral vectors are capable of infecting non-dividing cells and can be used for both in vivo and ex vivo gene transfer and expression of nucleic acid sequences. For example, recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference.

B. Regulatory Elements:

Vectors can also comprise other components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide.

Eukaryotic expression cassettes included in the vectors preferably contain (in a 5'-to-3' direction) a eukaryotic transcriptional promoter operably linked to a protein-coding sequence, splice signals including intervening sequences, and a transcriptional termination/polyadenylation sequence.

a. Promoter/Enhancers

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β-lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination (as per, for example, the Eukaryotic Promoter Data Base EPDB, http://www.epd.isb-sib.ch/) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

Non-limiting examples of promoters include early or late viral promoters, such as, SV40 early or late promoters, cytomegalovirus (CMV) immediate early promoters, Rous Sarcoma Virus (RSV) early promoters; eukaryotic cell promoters, such as, e.g., beta actin promoter (Ng, 1989, Quitsche et al., 1989), GADPH promoter (Alexander et al., 1988, Ercolani et al., 1988), metallothionein promoter (Karin et al., 1989; Richards et al., 1984); and concatenated response element promoters, such as cyclic AMP response element promoters (cre), serum response element promoter (sre), phorbol ester promoter (TPA) and response element promoters (tre) near a minimal TATA box. It is also possible to use human growth hormone promoter sequences (e.g., the human growth hormone minimal promoter described at Genbank, accession no. X05244, nucleotide 283-341) or a mouse mammary tumor promoter (available from the ATCC, Cat. No. ATCC 45007). A specific example could be a phosphoglycerate kinase (PGK) promoter.

b. Initiation Signals

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

C. Multiple Cloning Sites

Vectors can include a multiple cloning site (MCS), which is a nucleic acid region that contains multiple restriction enzyme sites, any of which can be used in conjunction with standard recombinant technology to digest the vector (see, for example, Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

d. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see, for example, Chandler et al., 1997, herein incorporated by reference.)

e. Termination Signals

The vectors or constructs of the present invention may comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

f. Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal or the bovine growth hormone polyadenylation signal, convenient and known to function well in various target cells. Polyadenylation may increase the stability of the transcript or may facilitate cytoplasmic transport.

C. Vector Delivery

Introduction of a reprogramming vector into somatic cells with the current invention may use any suitable methods for nucleic acid delivery for transformation of a cell, as described herein or as would be known to one of ordinary skill in the art. Such methods include, but are not limited to, direct delivery of DNA such as by ex vivo transfection (Wilson et al., 1989, Nabel et al, 1989), by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference; Tur-Kaspa et al., 1986; Potter et al., 1984); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988); by microprojectile bombardment (PCT Application Nos. WO 94/09699 and 95/06128; U.S. Pat. Nos. 5,610,042; 5,322,783, 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by *Agrobacterium*-mediated transformation (U.S. Pat. Nos. 5,591,616 and 5,563,055, each incorporated herein by reference); by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985), and any combination of such methods. Through the application of techniques such as these, organelle(s), cell(s), tissue(s) or organism(s) may be stably or transiently transformed.

a. Liposome-Mediated Transfection

In a certain embodiment of the invention, a nucleic acid may be entrapped in a lipid complex such as, for example, a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is a nucleic acid complexed with Lipofectamine (Gibco BRL) or Superfect (Qiagen). The amount of liposomes used may vary upon the nature of the liposome as well as the, cell used, for example, about 5 to about 20 µg vector DNA per 1 to 10 million of cells may be contemplated.

Liposome-mediated nucleic acid delivery and expression of foreign DNA in vitro has been very successful (Nicolau and Sene, 1982; Fraley et al., 1979; Nicolau et al., 1987). The feasibility of liposome-mediated delivery and expression of foreign DNA in cultured chick embryo, HeLa and hepatoma cells has also been demonstrated (Wong et al., 1980).

In certain embodiments of the invention, a liposome may be complexed with a hemagglutinating virus (HVJ). This has been shown to facilitate fusion with the cell membrane and promote cell entry of liposome-encapsulated DNA (Kaneda et al., 1989). In other embodiments, a liposome may be complexed or employed in conjunction with nuclear non-histone chromosomal proteins (HMG-1) (Kato et al., 1991). In yet further embodiments, a liposome may be complexed or employed in conjunction with both HVJ and HMG-1. In other embodiments, a delivery vehicle may comprise a ligand and a liposome.

b. Electroporation

In certain embodiments of the present invention, a nucleic acid is introduced into a cell via electroporation. Electroporation involves the exposure of a suspension of cells and DNA to a high-voltage electric discharge. Recipient cells can be made more susceptible to transformation by mechanical wounding. Also the amount of vectors used may vary upon the nature of the cells used, for example, about 5 to about 20 µg vector DNA per 1 to 10 million of cells may be contemplated.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

c. Calcium Phosphate

In other embodiments of the present invention, a nucleic acid is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

d. DEAE-Dextran

In another embodiment, a nucleic acid is delivered into a cell using DEAE-dextran followed by polyethylene glycol. In this manner, reporter plasmids were introduced into mouse myeloma and erythroleukemia cells (Gopal, 1985).

e. Sonication Loading

Additional embodiments of the present invention include the introduction of a nucleic acid by direct sonic loading. LTK-fibroblasts have been transfected with the thymidine kinase gene by sonication loading (Fechheimer et al., 1987).

f. Receptor Mediated Transfection

Still further, a nucleic acid may be delivered to a target cell via receptor-mediated delivery vehicles. These take advantage of the selective uptake of macromolecules by receptor-mediated endocytosis that will be occurring in a target cell. In view of the cell type-specific distribution of various receptors, this delivery method adds another degree of specificity to the present invention.

Certain receptor-mediated gene targeting vehicles comprise a cell receptor-specific ligand and a nucleic acid-binding agent. Others comprise a cell receptor-specific ligand to which the nucleic acid to be delivered has been operatively attached. Several ligands have been used for receptor-mediated gene transfer (Wu and Wu, 1987; Wagner et al., 1990; Perales et al., 1994; Myers, EPO 0273085), which establishes the operability of the technique. Specific delivery in the context of another mammalian cell type has been described (Wu and Wu, 1993; incorporated herein by reference). In certain aspects of the present invention, a ligand will be chosen to correspond to a receptor specifically expressed on the target cell population.

In other embodiments, a nucleic acid delivery vehicle component of a cell-specific nucleic acid targeting vehicle may comprise a specific binding ligand in combination with a liposome. The nucleic acid(s) to be delivered are housed within the liposome and the specific binding ligand is functionally incorporated into the liposome membrane. The liposome will thus specifically bind to the receptor(s) of a target cell and deliver the contents to a cell. Such systems have been shown to be functional using systems in which, for example, epidermal growth factor (EGF) is used in the receptor-mediated delivery of a nucleic acid to cells that exhibit upregulation of the EGF receptor.

In still further embodiments, the nucleic acid delivery vehicle component of a targeted delivery vehicle may be a liposome itself, which will preferably comprise one or more lipids or glycoproteins that direct cell-specific binding. For example, lactosyl-ceramide, a galactose-terminal asialganglioside, have been incorporated into liposomes and observed an increase in the uptake of the insulin gene by hepatocytes (Nicolau et al., 1987). It is contemplated that the tissue-specific transforming constructs of the present invention can be specifically delivered into a target cell in a similar manner.

g. Microprojectile Bombardment

Microprojectile bombardment techniques can be used to introduce a nucleic acid into at least one, organelle, cell, tissue or organism (U.S. Pat. No. 5,550,318; U.S. Pat. No. 5,538,880; U.S. Pat. No. 5,610,042; and PCT Application WO 94/09699; each of which is incorporated herein by reference). This method depends on the ability to accelerate DNA-coated microprojectiles to a high velocity allowing them to pierce cell membranes and enter cells without killing them (Klein et al., 1987). There are a wide variety of microprojectile bombardment techniques known in the art, many of which are applicable to the invention.

In this microprojectile bombardment, one or more particles may be coated with at least one nucleic acid and delivered into cells by a propelling force. Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold particles or beads. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. DNA-coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

VI. Selection of iPS Cells

In certain aspects of the invention, after a reprogramming vector is introduced into somatic cells, these cells will be cultured for expansion. Cells could be selected for the presence of vector elements like reporters or selection markers to concentrate transfected cells. Reprogramming vectors will express reprogramming factors in these cells and replicate and partition along with cell division. These expressed reprogramming factors will reprogram somatic cell genome to establish a self-sustaining pluripotent state, and in the meantime or after removal of positive selection of the presence of vectors, exogenous genetic elements will be lost gradually. This silencing of transgene expression permit selection of induced pluripotent stem cells for tuning off reporter gene expression alone or in combination with selection for other embryonic stem cell characteristics because they are expected to be substantially identical to pluripotent embryonic stem cells.

A. Selection for Reporter Gene Expression

Cells introduced with a reprogramming vector in this invention could express a reporter and a reprogramming factor simultaneously and selected for the presence or absence of reporter gene expression in different time points. For example, cells could be selected for the presence of reporters and transfection could be optimized by using reporters. Induced pluripotent stem cells may be screened for the loss of reporters as transgenes are silenced during reprogramming. Such selection or screen is based on a detectable signal generated by expression of reporter genes as a indication of transgene expression.

A detectable signal may be generated in any one of a number of ways, depending on the nature of the reporter gene employed in the method of the invention. For example, the detectable signal may be a luminescent, such as a fluorescent signal, e.g., GFP. GFP is a fluorescent polypeptide which produces a fluorescent signal without the need for a substrate or cofactors. GFP expression and detection techniques are well known in the art, and kits are available commercially, for example from Clontech. GFP expression may be assayed in intact cells without the need to lyse them or to add further reagents. Alternatively, the detectable signal may be a signal generated as a result of enzymatic activity or the recognition of a cell surface marker, e.g., LNGFR.

Flow cytometry, for example, fluorescence-activated cell sorting (FACS), is common to use to select for detectable signals based on reporter gene expression. FACS provides a method for sorting a heterogeneous mixture of cells into two or more containers, one cell at a time, based upon the specific light scattering and fluorescent characteristics of each cell. This provides fast, objective and quantitative recording of fluorescent signals from individual cells as well as physical separation of induced pluripotent cells.

Luciferase may also be used as a basis for an assay. Luciferase expression is known in the art, and luciferase expression and detection kits are available commercially from Clontech (Palo Alto, Calif.). The presence of luciferase is advantageously assessed by cell lysis and addition of luciferin substrate to the cells, before monitoring for a luminescent signal by scintillation counting.

Enzyme-based assays are conducted in a manner similar to a luciferase-based assay, except that the detection is not necessarily via luminescence. The detection technique will depend on the enzyme, and may therefore be optical (such as in the case of β-galactosidase).

Physical and biochemical methods may also be used to identify or quantify expression of the reporter genes of the present invention. These methods include but are not limited to: 1) Southern analysis or PCR amplification for detecting and determining the structure of the recombinant DNA insert; 2) northern blot, S-1 RNase protection, primer-extension or reverse transcriptase-PCR amplification for detecting and examining RNA transcripts of the gene constructs; 3) enzymatic assays for detecting enzyme activity, where such gene products are encoded by the gene construct; 4) protein gel electrophoresis, western blot techniques, immunoprecipitation, or enzyme-linked immunoassays, where the gene construct products are proteins; and 5) biochemical measurements of compounds produced as a consequence of the expression of the introduced gene constructs. Additional techniques, such as in situ hybridization, enzyme staining, and immunostaining, also may be used to detect the presence or expression of the reporter gene in specific cells.

B. Selection for Embryonic Stem Cell Characteristics

The successfully generated iPSCs from previous studies were remarkably similar to naturally-isolated pluripotent stem cells (such as mouse and human embryonic stem cells, mESCs and hESCs, respectively) in the following respects, thus confirming the identity, authenticity, and pluripotency of iPSCs to naturally-isolated pluripotent stem cells. Thus, induced pluripotent stem cells generated from the methods disclosed in this invention could be selected based on one or more of following embryonic stem cell characteristics in addition to presence or absence of reporter gene expression.

a. Cellular Biological Properties

Morphology:

iPSCs are morphologically similar to ESCs. Each cell may have round shape, large nucleolus and scant cytoplasm. Colonies of iPSCs could be also similar to that of ESCs. Human iPSCs form sharp-edged, flat, tightly-packed colonies similar to hESCs and mouse iPSCs form the colonies similar to mESCs, less flatter and more aggregated colonies than that of hESCs.

Growth Properties:

Doubling time and mitotic activity are cornerstones of ESCs, as stem cells must self-renew as part of their definition. iPSCs could be mitotically active, actively self-renewing, proliferating, and dividing at a rate equal to ESCs.

Stem Cell Markers:

iPSCs may express cell surface antigenic markers expressed on ESCs. Human iPSCs expressed the markers specific to hESC, including, but not limited to, SSEA-3, SSEA-4, TRA-1-60, TRA-1-81, TRA-2-49/6E, and Nanog. Mouse iPSCs expressed SSEA-1 but not SSEA-3 nor SSEA-4, similarly to mESCs.

Stem Cell Genes:

iPSCs may express genes expressed in undifferentiated ESCs, including Oct-3/4, Sox2, Nanog, GDF3, REX1, FGF4, ESG1, DPPA2, DPPA4, and hTERT.

Telomerase Activity:

Telomerases are necessary to sustain cell division unrestricted by the Hayflick limit of ~50 cell divisions. hESCs express high telomerase activity to sustain self-renewal and proliferation, and iPSCs also demonstrate high telomerase activity and express hTERT (human telomerase reverse transcriptase), a necessary component in the telomerase protein complex.

Pluripotency:

iPSCs will be capable of differentiation in a fashion similar to ESCs into fully differentiated tissues.

Neural Differentiation:

iPSCs could be differentiated into neurons, expressing βIII-tubulin, tyrosine hydroxylase, AADC, DAT, ChAT, LMX1B, and MAP2. The presence of catecholamine-associated enzymes may indicate that iPSCs, like hESCs, may be differentiable into dopaminergic neurons. Stem cell-associated genes will be downregulated after differentiation.

Cardiac Differentiation:

iPSCs could be differentiated into cardiomyocytes that spontaneously began beating. Cardiomyocytes expressed TnTc, MEF2C, MYL2A, MYHCβ, and NKX2.5. Stem cell-associated genes will be downregulated after differentiation.

Teratoma Formation:

iPSCs injected into immunodeficient mice may spontaneously formed teratomas after certain time, such as nine weeks. Teratomas are tumors of multiple lineages containing tissue derived from the three germ layers endoderm, mesoderm and ectoderm; this is unlike other tumors, which typically are of only one cell type. Teratoma formation is a landmark test for pluripotency.

Embryoid Body:

hESCs in culture spontaneously form ball-like embryo-like structures termed "embryoid bodies," which consist of a core of mitotically active and differentiating hESCs and a periphery of fully differentiated cells from all three germ layers. iPSCs may also form embryoid bodies and have peripheral differentiated cells.

Blastocyst Injection:

hESCs naturally reside within the inner cell mass (embryoblast) of blastocysts, and in the embryoblast, differentiate into the embryo while the blastocyst's shell (trophoblast) differentiates into extraembryonic tissues. The hollow trophoblast is unable to form a living embryo, and thus it is necessary for the embryonic stem cells within the embryoblast to differentiate and form the embryo. iPSCs injected by micropipette into a trophoblast to generate a blastocyst transferred to recipient females, may result in chimeric living mouse pups: mice with iPSC derivatives incorporated all across their bodies with 10%-90 and chimerism.

b. Epigenetic Reprogramming

Promoter Demethylation: Methylation is the transfer of a methyl group to a DNA base, typically the transfer of a methyl group to a cytosine molecule in a CpG site (adjacent cytosine/guanine sequence). Widespread methylation of a gene interferes with expression by preventing the activity of expression proteins or recruiting enzymes that interfere with expression. Thus, methylation of a gene effectively silences it by preventing transcription. Promoters of endogenous pluripotency-associated genes, including Oct-3/4, Rex1, and Nanog, may be demethylated in iPSCs, showing their promoter activity and the active promotion and expression of pluripotency-associated genes in iPSCs.

Histone Demethylation: Histones are compacting proteins that are structurally localized to DNA sequences that can effect their activity through various chromatin-related modifications. H3 histones associated with Oct-3/4, Sox2, and Nanog may be demethylated to activate the expression of Oct-3/4, Sox2, and Nanog.

VII. Culturing of iPS Cells

After somatic cells are introduced with a reprogramming vector using the disclosed methods, these cells may be cultured in a medium sufficient to maintain the pluripotency. Culturing of induced pluripotent stem (iPS) cells generated in this invention can use various medium and techniques developed to culture primate pluripotent stem cells, more specially, embryonic stem cells, as described in U.S. Pat. App. 20070238170 and U.S. Pat. App. 20030211603.

For example, like human embryonic stem (hES) cells, iPS cells can be maintained in 80% DMEM (Gibco #10829-018 or #11965-092), 20% defined fetal bovine serum (FBS) not heat inactivated, 1% non-essential amino acids, 1 mM L-glutamine, and 0.1 mM .beta.-mercaptoethanol. Alternatively, ES cells can be maintained in serum-free medium, made with 80% Knock-Out DMEM (Gibco #10829-018), 20% serum replacement (Gibco #10828-028), 1% non-essential amino acids, 1 mM L-glutamine, and 0.1 mM .beta.-mercaptoethanol. Just before use, human bFGF is added to a final concentration of .about 4 ng/mL (WO 99/20741).

IPS cells, like ES cells, have characteristic antigens that can be identified or confirmed by immunohistochemistry or flow cytometry, using antibodies for SSEA-1, SSEA-3 and SSEA-4 (Developmental Studies Hybridoma Bank, National Institute of Child Health and Human Development, Bethesda Md.), and TRA-1-60 and TRA-1-81 (Andrews et al., 1987). Pluripotency of embryonic stem cells can be confirmed by injecting approximately 0.5-10 10 6 cells into the rear leg muscles of 8-12 week old male SCID mice. Teratomas develop that demonstrate at least one cell type of each of the three germ layers.

VIII. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Construction of Retroviral Vectors

The parental retroviral vector for which the reprogramming genes and selection markers were introduced has previously been cited in Kennedy et al. (2003). Briefly, the minimal vector contains the 5' and 3' MMLV long terminal repeat region (LTR) in which the 5' LTR contains the promoter used to drive the expression of the genes required for reprogramming and selection (FIG. 1). Conveniently, there is also a cytomegalovirus promoter located just upstream of the 5' LTR so that the retroviral plasmids can be used for transient transfection yet will remain nonfunctional when the plasmid is used as a template for viral synthesis.

As indicated in FIG. 1, Sox-2, Nanog, Oct4, and Lin28 were each introduced into an MMLV-based retroviral backbone also encoding a fluorescent protein. Both Sox-2 and Oct4 were placed into retroviral backbones encoding expression for enhanced green fluorescent protein (eGFP) while Nanog and Lin28 were placed into backbones competent to express monomeric red fluorescent protein (mRFP). The translation of transcripts encoding the genes for reprogramming initiate at a canonical ATG start codon while the downstream fluorescent protein is translated via an internal ribosome entry site (IRES) derived from the encephalomyocarditis virus.

Example 2

Generation of Virus Using the Retroviral Vectors

The retroviral vectors were used in the following way to generate virus. First, each of the four retroviral vectors encoding Sox-2, Oct4, Nanog, or Lin-28 were prepared as separate transfections. Ten micrograms of each retroviral vector were mixed separately with DNA encoding Vesicular Stomatitis Virus-pseudotyped glycoprotein (1 μg), Gag polymerase (3 ug), and NFkB (1 ug). The DNA was then mixed with 500 ul of OptiMem. Separately, 40 microliters of polyethylenimine (1 mg/ml) were mixed with 500 μl OptiMem. The DNA/OptiMem mixture and PEI/OptiMem mixture were then left to incubate at room temperature for 5 minutes then combined to yield approximately 1 ml of solution that must be incubated for at least 20 minutes at room temperature.

The inventors transfect 293 cells overexpressing the SV40 T-antigen protein that were split one day prior to transfection at a dilution that allows cells to be approximately 80 percent confluent on the day of transfection. On the day of transfection, the cells were washed with 1×PBS and 4 ml of OptiMem or DMEM (serum and antibiotic-free) is then added. Once lypophyllic complexes had formed during the 20 minute incubation period, the DNA complex (1 ml) was then added dropwise to the cells. The media was replaced 4 hours following incubation at 37° C. with DMEM, 10% fetal bovine or calf serum, and 50 mM Hepes buffered saline. Virus was harvested 48 hours post-transfection by collecting the 5 ml of media from the transfected plates. The virus-containing media was then spun down for 5 minutes at 1000 rpm to remove cell debris, and the media is filtered through a 45 um syringe filter.

Example 3

Infection and Plating of Cells

The procedure involving infection and transition to an environment that allows for reprogramming to take place occurred following one of two methods. One method involved infection and plating of infected and uninfected cells onto irradiated MEFs for reprogramming, and the other method involved plating only infected cells by way of sorting onto MEFs in an effort to enhance the efficiency of reprogramming.

Method 1: Reprogramming Unsorted IMR-90 Cells Infected with Virus Expressing Reprogramming Genes IMR-90 cells have been used successfully as the recipient host for infection, but this protocol is adaptable to the infection of alternative cell types such as primary skin cells and hematopoietic cells. Approximately 50,000 IMR-90 cells were seeded into each well of a 6-well plate 72 hours prior to infection. An additional plate of cells was prepared for use in determining the efficiency of infection for each of the viruses. For example, one well of cells became the recipient for a single virus rather than multiple viruses. Infections were performed at a multiplicity of infection (MOI) ranging from 1 to 10 with virus harvested fresh from transfected 293T cells. The range in MOI is due to the inherent variability from transfection to transfection for the production of virus.

The infection took place within the 6-well plate by first removing the media and replacing with an equal volume of each of the four viruses for a final concentration of approximately $5 \times 10^4$ to $1 \times 10^5$ cells per ml of medium (i.e., 500 μl for each virus for a final volume of 2 ml). Cells remained adherent and were placed on a rocking platform at 4° C. for 2 hours and placed at 37° C. and 5% $CO_2$. Alternatively, cells could be placed immediately into the incubator without a significant effect on the efficiency of infection. The day of infection was considered timepoint 0 and every day thereafter considered post-infection. Infected cells were then incubated for 48 hours at which time cells from each well of a 6-well plate infected with all four viruses were harvested with 0.2 to 0.5 ml of 0.05% Trypsin-EDTA. Cells were collected, pooled, and brought to volume with 10-15 ml Minimal Essential Media with 10% FBS (M10F). They were then spun at 1000 rpm for 5 minutes, the supernatant was removed, and cells were resuspended in 10 ml of M10F without antibiotic and plated on top of a monolayer of irradiated mouse embryonic fibroblasts (MEFs).

The MEFs were plated onto a 10 cm plate coated with 0.1% gelatin 3 days prior to the addition of infected IMR-90 cells at a density of approximately $7.5 \times 10^4$ cells/ml. The day following MEF plating, the media was removed and replaced with human ES (hES) media without FGF (80% DMEM-F12; 20% Knock-out Serum Replacer; 1% Non-essential amino acids; 1 mM L-glutamine; 0.1 mM b-mercaptoethanol). On day 3 after plating, MEFs were washed once with 1×PBS (Ca and Mg-free) and infected IMR-90 cells resuspended in 10 ml M10F were placed over the MEFs. An overnight incubation allowed IMR-90 cells to adhere, and the medium was replaced with 10 ml of Conditioned Media (CM) containing 100 ng/ml of zebrafish FGF (represents 3 days post-infection). CM was prepared by incubating hES media on a bed of high-density irradiated MEFs overnight, collecting, and supplementing with 100 ng/ml zFGF. The infected IMR-90 cells were then fed daily by replacing the spent media with 10 ml of fresh CM with zFGF.

Method 2: Reprogramming Sorted IMR-90 Cells Infected with Virus Expressing Reprogramming Genes Infections were performed as indicated in Method 1 with the exception that two, complete, 6-well plates were seeded with $5 \times 10^4$ IMR-90 cells per well prior to infection. A larger pool of infected cells facilitates sorting as well as enhances viability following sorting. In preparation for sorting, all wells containing IMR-90 cells were harvested by trypsin and pooled as indicated in Method 1 3 days post-infection. Pooled cells were filtered to remove clumps and maintained on ice until sorting.

A FACs DIVA at a pressure of 25 psi with a tip size measuring 10 microns was used to sort selected cells into a 15 ml conical tube containing M20F/50 mM Hepes buffer. Sorting was based on low to moderate levels of eGFP which correlated with the levels of Oct4 and Sox-2 expression and low to moderate levels of mRFP correlating with levels of Nanog and Lin28. The inventors have also performed this experiment in the absence of Lin28 in which case cells expressing varying levels of Nanog could be specifically sorted. The efficiency of reprogramming correlates with increasing amounts of Nanog and therefore cells expressing moderate to high levels of Nanog, reflected by mRFP intensity, were sorted.

On average, approximately 85% of IMR-90 cells were infected with each virus according to the fraction of cells positive for eGFP or mRFP as determined by FACs and about $3 \times 10^4$ to $2 \times 10^5$ cells were collected. Cells were maintained on ice and chilled during sorting until they were plated. On the same day, the sorted cells were brought to a total volume of 10 ml of M10F then placed on a monolayer of irradiated MEFs plated 1-6 days prior at a density of approximately $7.5 \times 10^4$ cells/ml. The cells were cultured on MEFs in M10F (no antibiotic) for 3 more days to allow for recovery and attachment post-sorting. (MEFs were prepared as described in Method 1). At 6 days following infection, 10 ml CM supplemented with 100 ng/ml of zebrafish FGF was used in place of M10F and replenished daily until reprogrammed colonies formed.

Example 4

Selection of Reprogrammed Cells

Reprogrammed cells were initially identified by morphology as well as a loss of eGFP and mRFP expression. Colonies contained highly compact cells with enlarged nuclei and multiple nucleoli. Currently, the inventors have picked colonies within a timeframe ranging from 20 to 40 days after infection. Colonies were picked by hand and transferred to a well (48, 24, to 6 well) containing irradiated MEFs ($7.5 \times 10^4$ cells/ml). They were left unfed the day following transfer then feeding with CM resumed daily until colonies expanded in numbers sufficient for splitting and freezing. iPS clones were further characterized using cell surface markers (i.e., SSEA 3, SSEA 4, Tra-1-60, SSEA 1, and Oct4) as well as karyotyped to identify any abnormalities within the chromosomes.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,683,202
U.S. Pat. No. 4,684,611
U.S. Pat. No. 4,952,500
U.S. Pat. No. 5,302,523
U.S. Pat. No. 5,322,783
U.S. Pat. No. 5,384,253
U.S. Pat. No. 5,464,765
U.S. Pat. No. 5,538,877
U.S. Pat. No. 5,538,880
U.S. Pat. No. 5,550,318
U.S. Pat. No. 5,563,055
U.S. Pat. No. 5,580,859
U.S. Pat. No. 5,589,466
U.S. Pat. No. 5,591,616
U.S. Pat. No. 5,610,042
U.S. Pat. No. 5,656,610
U.S. Pat. No. 5,702,932
U.S. Pat. No. 5,736,524
U.S. Pat. No. 5,780,448
U.S. Pat. No. 5,789,215
U.S. Pat. No. 5,925,565
U.S. Pat. No. 5,928,906
U.S. Pat. No. 5,935,819
U.S. Pat. No. 5,945,100
U.S. Pat. No. 5,981,274
U.S. Pat. No. 5,994,136
U.S. Pat. No. 5,994,624
U.S. Pat. No. 5,981,274
U.S. Pat. No. 5,945,100
U.S. Pat. No. 5,780,448
U.S. Pat. No. 5,736,524
U.S. Pat. No. 5,702,932
U.S. Pat. No. 5,656,610
U.S. Pat. No. 5,589,466
U.S. Pat. No. 5,580,859
U.S. Pat. No. 6,013,516
U.S. Patent Appln. 20030211603
U.S. Patent Appln. 20070238170
Alexander et al., *Proc. Nat. Acad. Sci. USA*, 85:5092-5096, 1988.
Andrews et al., In: *Teratocarcinomas and Embryonic Stem Cells*, Robertson (Ed.), IRL Press, 207-246, 1987.
Ausubel et al., *Current Protocols in Molecular Biology*, Greene Publ. Assoc. Inc. & John Wiley & Sons, Inc., MA, 1994.
Blomer et al., *J. Virol.*, 71(9):6641-6649, 1997.
Boyer et al., *Cell*, 122(6):947-56, 2005.
Carbonelli et al., *FEMS Microbiol. Lett.*, 177(1):75-82, 1999.
Chalfie et al., *Science*, 263(5148):802-805, 1994.
Chambers et al., *Cell*, 113(5):643-55, 2003.
Chandler et al., *Proc. Natl. Acad. Sci. USA*, 94(8):3596-601, 1997.
Chen and Okayama, *Mol. Cell. Biol.*, 7(8):2745-2752, 1987.
Cocea, *Biotechniques*, 23(5):814-816, 1997.
EPO 0273085
Ercolani et al., *J. Biol. Chem.*, 263: 15335-15341, 1988.
Fechheimer et al., *Proc Natl. Acad. Sci. USA*, 84:8463-8467, 1987.
Fraley et al., *Proc. Natl. Acad. Sci. USA*, 76:3348-3352, 1979.
Ghosh and Bachhawat Gopal, 1985
Gopal, *Mol. Cell. Biol.*, 5:1188-1190, 1985.
Graham and Van Der Eb, *Virology*, 52:456-467, 1973.
Harland and Weintraub, *J. Cell Biol.*, 101(3):1094-1099, 1985.
Jaenisch, *Science* 240:1468-1474, 1988.
Kaeppler et al., *Plant Cell Reports*, 9:415-418, 1990.
Kaneda et al., *Science*, 243:375-378, 1989.
Karin et al., *Cell*, 36:371-379, 1989.
Kato et al, *J. Biol. Chem.*, 266:3361-3364, 1991.
Kennedy et al., *Proc. Natl. Acad. Sci. USA*, 100:14269-14274, 2003.
Kim et al., *Molec. Cellular Biol.*, 12(8):3636-3643, 1992.
Klein et al., *Nature*, 327:70-73, 1987.
Levenson et al., *Hum. Gene Ther.*, 9(8):1233-1236, 1998.
Macejak and Sarnow, *Nature*, 353:90-94, 1991.
Mann et al., *Cell*, 33:153-159, 1983.
McBratney, et al., *Curr. Opin. Cell Biol.*, 5:961-965, 1993.
Miller et al., *Am. J. Clin. Oncol.*, 15(3):216-221, 1992.
Nabel et al., *Science*, 244(4910):1342-1344, 1989.
Naldini et al., *Science*, 272(5259):263-267, 1996.
Ng, *Nuc. Acid Res.*, 17:601-615, 1989.
Nicolas and Rubinstein, In: *Vectors: A survey of molecular cloning vectors and their uses*, Rodriguez and Denhardt, eds., Stoneham: Butterworth, 494-513, 1988.
Nicolau and Sene, *Biochim. Biophys. Acta*, 721:185-190, 1982.
Nicolau et al., *Methods Enzymol.*, 149:157-176, 1987.
Omirulleh et al., *Plant Mol. Biol.*, 21(3):415-428, 1993.
Paskind et al., *Virology*, 67:242-248, 1975.
Pelletier and Sonenberg, *Nature*, 334(6180):320-325, 1988.
Perales et al., *Proc. Natl. Acad. Sci. USA*, 91:4086-4090, 1994.
Potrykus et al., *Mol. Gen. Genet.*, 199(2):169-177, 1985.
Potter et al., *Proc. Natl. Acad. Sci. USA*, 81:7161-7165, 1984.
Quitsche et al., *J. Biol. Chem.*, 264:9539-9545, 1989.
Richards et al., *Cell*, 37:263-272, 1984.
Rippe, et al., *Mol. Cell. Biol.*, 10:689-695, 1990.
Sambrook et al., In: *Molecular cloning: a laboratory manual*, $2^{nd}$ Ed., Cold Spring Harbor Laboratory Press, Cold Spring Harbor, N.Y., 1989.

Sambrook and Russell, Molecular Cloning: A Laboratory Manual 3$^{rd}$ Ed., Cold Spring Harbor Laboratory Press, 2001.
Takahashi et al., *Cell,* 126(4):663-676, 2006.
Takahashi et al., *Cell,* 126(4):663-76, 2007.
Temin, In: *Gene Transfer,* Kucherlapati (Ed.), NY, Plenum Press, 149-188, 1986.
Tur-Kaspa et al., *Mol. Cell. Biol.,* 6:716-718, 1986.
Wagner et al., *Proc. Natl. Acad. Sci. USA* 87(9):3410-3414, 1990.
Wilson et al., *Science,* 244:1344-1346, 1989.
WO 94/09699
WO 95/06128
WO 99/20741
Wong et al., *Gene,* 10:87-94, 1980.
Wu and Wu, *Adv. Drug Delivery Rev.,* 12:159-167, 1993.
Wu and Wu, *Biochemistry,* 27: 887-892, 1988.
Wu and Wu, *J. Biol. Chem.,* 262:4429-4432, 1987.
Wu et al., *J. Virol.,* 76(5):2480-2490, 2002.
Yamanaka et al., *Cell,* 131(5):861-72, 2007.
Yang and Russell, *Proc. Natl. Acad. Sci. USA,* 87:4144-4148, 1990.
Yu et al., *Science,* 318:1917-1920, 2007.
Zufferey et al., *Nat. Biotechnol.,* 15(9):871-875, 1997.

What is claimed is:

1. A reprogramming vector comprising a polycistronic expression cassette, wherein the polycistronic expression cassette comprises a transcriptional regulatory element; and a first and second coding sequence operably linked to said transcriptional regulatory element, wherein said first coding sequence encodes a first reprogramming factor and said second coding sequence encodes a second reprogramming factor, wherein the reprogramming vector is an Epstein-Barr Virus (EBV)-based vector, and further wherein the first and second reprogramming factor are selected from the group consisting of Sox, Oct, Nanog, Lin28, Klf4, and c-Myc.

2. The reprogramming vector of claim 1, wherein said expression cassette further comprises a third coding sequence operably linked to said transcriptional regulatory element, wherein said third coding sequence encodes a reprogramming factor, a reporter, or a selection marker.

3. The reprogramming vector of claim 2, wherein the third coding sequence encodes a selection marker.

4. The reprogramming vector of claim 3, wherein the selection marker is an antibiotic resistance marker.

5. The reprogramming vector of claim 2, wherein said reporter is a cell surface marker, a fluorescent protein, an epitope, chloramphenicol acetyl transferase (CAT), luciferase or β-galactosidase.

6. The reprogramming vector of claim 5, wherein said fluorescent protein is a green fluorescent protein (GFP), red fluorescent protein (RFP), blue fluorescent protein (BFP) or yellow fluorescent protein (YFP).

7. The reprogramming vector of claim 1, wherein Sox is Sox-1, Sox-2, Sox-3, Sox-15, or Sox-18.

8. The reprogramming vector of claim 1, wherein Oct is Oct-4.

9. The reprogramming vector of claim 1, wherein said first or second reprogramming factor is Nanog, Lin28, Klf4, or c-Myc.

10. The reprogramming vector of claim 1, wherein the expression cassette further comprises one or more IRES.

11. The reprogramming vector of claim 10, wherein said IRES is selected from the group consisting of an encephalomyocarditis virus IRES, a picornavirus IRES, a foot-and-mouth disease virus IRES, a hepatitis A virus IRES, a hepatitis C virus IRES, a human rhinovirus IRES, a poliovirus IRES, a swine vesicular disease virus IRES, a turnip mosaic potyvirus IRES, a human fibroblast growth factor 2 mRNA IRES, a pestivirus IRES, a *Leishmania* RNA virus IRES, a Moloney murine leukemia virus IRES a human rhinovirus 14 IRES, an aphthovirus IRES, a human immunoglobulin heavy chain binding protein mRNA IRES, a *Drosophila* Antennapedia mRNA IRES, a human fibroblast growth factor 2 mRNA IRES, a hepatitis G virus IRES, a tobamovirus IRES, a vascular endothelial growth factor mRNA IRES, a Coxsackie B group virus IRES, a c-myc protooncogene mRNA IRES, a human MYT2 mRNA IRES, a human parechovirus type 1 virus IRES, a human parechovirus type 2 virus IRES, a eukaryotic initiation factor 4GI mRNA IRES, a *Plautia stali* intestine virus IRES, a Theiler's murine encephalomyelitis virus IRES, a bovine enterovirus IRES, a connexin 43 mRNA IRES, a homeodomain protein Gtx mRNA IRES, an AML1 transcription factor mRNA IRES, an NF-kappa B repressing factor mRNA IRES, an X-linked inhibitor of apoptosis mRNA IRES, a cricket paralysis virus RNA IRES, a p58 (PITSLRE) protein kinase mRNA IRES, an ornithine decarboxylase mRNA IRES, a connexin-32 mRNA IRES, a bovine viral diarrhea virus IRES, an insulin-like growth factor I receptor mRNA IRES, a human immunodeficiency virus type 1 gag gene IRES, a classical swine fever virus IRES, a Kaposi's sarcoma-associated herpes virus IRES, a short IRES selected from a library of random oligonucleotides, a Jembrana disease virus IRES, an apoptotic protease-activating factor 1 mRNA IRES, a *Rhopalosiphum padi* virus IRES, a cationic amino acid transporter mRNA IRES, a human insulin-like growth factor II leader 2 mRNA IRES, a giardiavirus IRES, a Smad5 mRNA IRES, a porcine teschovirus-1 talfan IRES, a *Drosophila* Hairless mRNA IRES, an hSNM1 mRNA IRES, a Cbfa1/Runx2 mRNA IRES, an Epstein-Barr virus IRES, a hibiscus chlorotic ringspot virus IRES, a rat pituitary vasopressin V1b receptor mRNA IRES, and a human hsp70 mRNA IRES.

12. The reprogramming vector of claim 11, wherein the IRES is an encephalomyocarditis virus IRES.

13. A method for producing a human induced pluripotent stem (iPS) cell population, the method comprising the steps of:
(a) obtaining one or more reprogramming vectors according to claim 4; and
(b) introducing the reprogramming vectors into human cells of a population of human somatic cells to provide the human iPS cell population.

14. The method of claim 13, further comprising the step of:
(c) culturing the human cells into which the one or more reprogramming vectors have been introduced to expand the population; and
(d) selecting progeny cells of said expanded population, wherein said progeny cells have one or more characteristics of human embryonic stem cells.

15. The method of claim 13, wherein said one or more reprogramming vectors include coding sequences that encode reprogramming factors comprising Sox and Oct.

16. The method of claim 13, wherein said one or more reprogramming vector is introduced into said cells by liposome transfection, electroporation, particle bombardment, calcium phosphate, polycation, or polyanion.

17. The method of claim 13, wherein the human somatic cells are human fibroblasts, hematopoietic cells, or mesenchymal cells.

18. The method of claim 17, wherein the human somatic cells are human fibroblasts.

19. The method of claim 14, wherein said characteristic is an essential loss of expression of said reporter.

20. The method of claim 14, wherein said characteristic is selected by fluorescence-activated cell sorting (FACS), CAT assay or luminescence assay.

21. The method of claim 14, wherein said characteristic is an undifferentiated morphology.

22. The method of claim 14, wherein said characteristic is one or more embryonic stem cell-specific markers selected from the group consisting of SSEA-3, SSEA-4, Tra-1-60 or Tra-1-81, Tra-2-49/6E, GDF3, REX1, FGF4, ESG1, DPPA2, DPPA4, and hTERT.

* * * * *